US010159715B2

(12) United States Patent
Kim et al.

(10) Patent No.: US 10,159,715 B2
(45) Date of Patent: Dec. 25, 2018

(54) METHOD FOR TREATING DIABETES COMPRISING LONG-ACTING INSULIN ANALOGUE CONJUGATE AND LONG-ACTING INSULINOTROPIC PEPTIDE CONJUGATE

(71) Applicant: HANMI PHARM. CO., LTD., Hwaseong-si, Gyeonggi-do (KR)

(72) Inventors: Jung Kuk Kim, Hwaseong-si (KR); Dae Jin Kim, Hwaseong-si (KR); Yong Ho Heo, Seongnam-si (KR); In Young Choi, Yongin-si (KR); Sung Youb Jung, Yongin-si (KR); Se Chang Kwon, Gangnam-gu (KR)

(73) Assignee: HANMI PHARM. CO., LTD, Hwaseong-si (KR)

( * ) Notice: Subject to any disclaimer, the term of this patent is extended or adjusted under 35 U.S.C. 154(b) by 0 days.

(21) Appl. No.: 15/313,501

(22) PCT Filed: May 29, 2015

(86) PCT No.: PCT/KR2015/005424
§ 371 (c)(1),
(2) Date: Nov. 22, 2016

(87) PCT Pub. No.: WO2015/183038
PCT Pub. Date: Dec. 3, 2015

(65) Prior Publication Data

US 2017/0143802 A1 May 25, 2017

(30) Foreign Application Priority Data

May 29, 2014 (KR) ........................ 10-2014-0065072

(51) Int. Cl.

| | |
|---|---|
| ***A61K 38/26*** | (2006.01) |
| ***A61K 38/28*** | (2006.01) |
| ***A61K 47/30*** | (2006.01) |
| ***C07K 16/28*** | (2006.01) |
| ***A61K 47/60*** | (2017.01) |
| ***A61K 47/50*** | (2017.01) |
| ***A61K 47/68*** | (2017.01) |

(52) U.S. Cl.
CPC .............. *A61K 38/28* (2013.01); *A61K 38/26* (2013.01); *A61K 47/30* (2013.01); *A61K 47/50* (2017.08); *A61K 47/60* (2017.08); *A61K 47/6849* (2017.08); *C07K 16/283* (2013.01)

(58) Field of Classification Search
CPC .. A61K 38/26; A61K 38/28; A61K 47/48215; A61K 47/48561
See application file for complete search history.

(56) References Cited

U.S. PATENT DOCUMENTS

| | | | |
|---|---|---|---|
| 5,175,145 | A | 12/1992 | Cooper |
| 5,422,339 | A | 6/1995 | Eisenbarth et al. |
| 5,424,286 | A | 6/1995 | Eng |
| 6,403,764 | B1 | 6/2002 | Dubaquie et al. |
| 7,736,653 | B2 | 6/2010 | Kim et al. |
| 7,790,677 | B2 | 9/2010 | Zimmerman et al. |
| 8,476,230 | B2 | 7/2013 | Song et al. |
| 9,165,768 | B2 | 10/2015 | Kang |
| 9,341,445 | B2 | 5/2016 | De Haas et al. |
| 9,422,349 | B2 | 8/2016 | Jung et al. |
| 9,526,764 | B2 | 12/2016 | Werner et al. |
| 9,528,180 | B2 | 12/2016 | Becker et al. |
| 9,669,073 | B2 | 6/2017 | Kim et al. |
| 2005/0288248 | A1 | 12/2005 | Pan et al. |

(Continued)

FOREIGN PATENT DOCUMENTS

| | | |
|---|---|---|
| CL | 1235-2003 | 4/2004 |
| CL | 00018-2009 | 6/2009 |

(Continued)

OTHER PUBLICATIONS

Intellectual Property Office of Singapore, Communication dated Oct. 3, 2017 in counterpart application No. 11201609564T.
European Patent Office, Communication dated Nov. 10, 2017 in counterpart application No. 15799334.6.
Fosgerau et al., "Combination of Long-Acting Insulin with the Dual GluGLP-1 Agonist ZP2929 Causes Improved Glycemic Control without Body Weight Gain in db/db Mice", 1527-P, Diabetes (Suppl 1), vol. 60, 2011, p. A418, XP-002775063.
European Patent Office; Communication dated Nov. 17, 2017 in counterpart application No. 15799077.1.

(Continued)

*Primary Examiner* — Gyan Chandra
(74) *Attorney, Agent, or Firm* — Sughrue Mion, PLLC

(57) ABSTRACT

The present invention relates to a composition for the prevention or treatment of diabetes including a long-acting insulin conjugate and a long-acting insulinotropic peptide conjugate, and a method for treating diabetes. More specifically, combination administration of the long-acting analog conjugate and the long-acting insulinotropic peptide conjugate inhibits weight gain due to administration of insulin, and vomiting and nausea due to administration of the insulinotropic peptide, and also reduces the required doses of insulin, thereby remarkably improving drug compliance. In addition, the present invention relates to administering a pharmaceutical composition for reducing side effects of pancreatic beta cells in diabetic patients, including a long-acting insulin analog conjugate and a long-acting insulinotropic peptide analog conjugate, and to a method for reducing side effects of pancreatic beta cells in diabetic patients, including the step of administering the composition. Specifically, the present invention is characterized in reducing side effects such as abnormality in the function of pancreatic beta cells associated with the development of diabetes, reduction in the pancreatic beta cell mass, lipotoxicity, or glucotoxicity.

21 Claims, 5 Drawing Sheets

Specification includes a Sequence Listing.

(56) References Cited

U.S. PATENT DOCUMENTS

| | | | | |
|---|---|---|---|---|
| 2006/0241019 | A1 | 10/2006 | Bridon et al. | |
| 2010/0105877 | A1 | 4/2010 | Song et al. | |
| 2010/0216692 | A1 | 8/2010 | Brunner-Schwarz et al. | |
| 2011/0077197 | A1 | 3/2011 | Habermann et al. | |
| 2011/0152185 | A1 | 6/2011 | Plum et al. | |
| 2011/0257091 | A1* | 10/2011 | DiMarchi | C07K 14/62 514/6.2 |
| 2012/0021978 | A1 | 1/2012 | Werner et al. | |
| 2012/0071402 | A1 | 3/2012 | Madsen et al. | |
| 2012/0100141 | A1 | 4/2012 | Herring et al. | |
| 2012/0184488 | A1 | 7/2012 | Weiss | |
| 2013/0028918 | A1 | 1/2013 | Song et al. | |
| 2013/0122023 | A1 | 5/2013 | Woo et al. | |
| 2014/0120120 | A1 | 5/2014 | Woo et al. | |
| 2014/0212440 | A1 | 7/2014 | Jung et al. | |
| 2015/0190528 | A1* | 7/2015 | Lim | A61K 47/22 424/179.1 |
| 2016/0008483 | A1 | 1/2016 | Hwang et al. | |
| 2017/0143802 | A1 | 5/2017 | Kim et al. | |

FOREIGN PATENT DOCUMENTS

| | | | |
|---|---|---|---|
| CL | 201603075 | | 11/2016 |
| DE | 102 27 232 | A1 | 1/2004 |
| DE | 10 2008 003 568 | A2 | 7/2009 |
| DE | 10 2008 025 008 | A1 | 11/2009 |
| EP | 2017288 | A1 | 1/2009 |
| EP | 2700654 | A1 | 2/2014 |
| EP | 2963056 | A1 | 1/2016 |
| JP | 2012-62311 | A | 3/2012 |
| JP | 2012-229214 | A | 11/2012 |
| KR | 10-2005-0121748 | A | 12/2005 |
| KR | 10-0725315 | B1 | 6/2007 |
| KR | 10-0725315 | B1 | 6/2007 |
| KR | 10-2010-0111683 | A | 10/2010 |
| KR | 10-2011-0111267 | A | 1/2011 |
| KR | 2011-0084956 | A | 7/2011 |
| KR | 10-1058209 | B1 | 8/2011 |
| KR | 10-1058290 | B1 | 8/2011 |
| KR | 2011-0092253 | A | 8/2011 |
| KR | 10-2011-0134209 | A | 12/2011 |
| KR | 10-2011-0134210 | A | 12/2011 |
| KR | 10-2012-00137271 | A | 12/2012 |
| KR | 10-2012-0139579 | A | 12/2012 |
| KR | 10-1231431 | B1 | 2/2013 |
| KR | 2011-137819 | A | 6/2013 |
| KR | 10-1324828 | B1 | 11/2013 |
| KR | 10-1330868 | B1 | 11/2013 |
| KR | 10-1330868 | B1 | 11/2013 |
| KR | 2014-0006938 | A | 1/2014 |
| KR | 2014-0022909 | A | 2/2014 |
| KR | 2012-0135123 | A | 7/2014 |
| KR | 10-2014-0106452 | A | 9/2014 |
| TW | 201204382 | A1 | 2/2012 |
| WO | WO-96/32478 | A1 | 10/1996 |
| WO | WO-97/34631 | A1 | 9/1997 |
| WO | 2009/129250 | A2 | 10/2009 |
| WO | 2010/080606 | A1 | 7/2010 |
| WO | 2010/080609 | A1 | 7/2010 |
| WO | 2011/028813 | A2 | 3/2011 |
| WO | 2011/122921 | A2 | 10/2011 |
| WO | 2012/015692 | A2 | 2/2012 |
| WO | 2012/098462 | A1 | 7/2012 |
| WO | 2012/165915 | A2 | 12/2012 |
| WO | 2012/167251 | A1 | 12/2012 |
| WO | 2012/169798 | A2 | 12/2012 |
| WO | 2012/173422 | A1 | 12/2012 |
| WO | 2013/110069 | A1 | 7/2013 |
| WO | 2013/133667 | A1 | 9/2013 |
| WO | 2014/017843 | A1 | 1/2014 |
| WO | 2014/017845 | A2 | 1/2014 |
| WO | 2014/017847 | A1 | 1/2014 |
| WO | 2014/017849 | A1 | 1/2014 |
| WO | 2014/049610 | A2 | 4/2014 |
| WO | 2014/073842 | A1 | 5/2014 |
| WO | 2014/133324 | A1 | 9/2014 |
| WO | 2015/183038 | A1 | 12/2015 |

OTHER PUBLICATIONS

United States Patent and Trademark Office communication dated Sep. 14, 2017 in counterpart U.S. Appl. No. 15/250,459.

UniProtKB A6XGL2, pp. 1-5. Integrateded in UniProtKB/TrEMBL Aug. 21, 2007.

Yampolsky et al., "The Exchangeability of Amino Acids in Proteins," Genetics, 170: 1459-1472, 2005.

Rudinger J., "Characteristics of the Amino Acids as Components of a Peptide Hormone Sequence," Peptide Hormones, J.A. Parsons Edition, University Park Press, Jun. 1976, pp. 1-7. (8 pages total).

"Designing Custom Peptides," from SIGMA Genosys, pp. 1-2. Accessed Dec. 16, 2004.

Schinzel R., Drueckes P., "The Phosphate Recognition Site of *Escherichia coli* Maltodextrin Phosphorylase," FEBS, Jul. 1991. 286(1,2): 125-128.

Berendsen HJC, "A Glimpse of the Holy Grail?" Science, 1998, 282: 642-643.

Voet D, Voet JG, Biochemistry, Second Edition, John Wiley & Sons, Inc., 1995, pp. 235-241. (9 pages).

Ngo J.T., Marks J, Karplus M., "Computational Complexity, Protein Structure Prediction, and the Levinthal Paradox," The Protein Folding Problem and Teritary Structure Prediction, K. Merc Jr. and S. Le Grand Edition, 1994, pp. 491-495.

Bradley CM, Barrick D, "Limits of Cooperativity in a Structurally Modular Protein: Response of the Notch Ankyrin Domain to Analogous Alanine Substitutions in Each Repeat," J. Mol. Biol., 2002, 324: 373-386.

Betts et al., "Amino Acid Properties and Consequences of Substitutions," Bioinformatics for Geneticists, Chapter 14, John Wiley & Sons, LTd., 2003, pp. 289-316.

Jørgensen, A. et al (Apr. 1996). "Solution Structure of the Superactive Monomeric Des-[Phe(B25)] Human Insulin Mutant: Elucidation of the Structural Basis for the Monomerization of Des-[Phe(B25)] Insulin and the Dimerization of Native Insulin," 257(3):684-699.

Keller, D. et al. (2001). "Flexibility and Bioactivity of Insulin: an NMR Investigation of the Solution Structure and Folding of an Unusually Flexible Human Insulin Mutant with Increased Biological Activity," Biochemistry 40(35):10732-10740.

NCBI, Genbank AAA72172.1, (Apr. 27, 1993)/ "Synthetic Preproinsulin [synthetic construct] NCBI," located at https://www.ncbi.nlm.nih.gov/protein/AAA72172.1?report=gpwithparts&log$=seqview, last visited on Jun. 20, 2017.

NCBI, Genbank AKI70564.1 (Jun. 1, 2015). "INS, Partial [synthetic construct]" located at <https://www.ncbi.nlm.nih.gov/protein/AKI70564.1?report=gpwithparts&log$=seqview> last visited on Jun. 20, 2017.

NCBI, Genbank NM 001291897.1, (May 13, 2015). "*Homo sapiens* Insulin (INS), Transcript Variant 4, mRNA," located at <https://www.ncbi.nlm.nih.gov/nuccore/NM-001291897.1?report=gpwithparts&log$=seqview&sat=4&satkey=139944924>, last visited on Jun. 20, 2017, 4 pages.

Uhlman, E. et al. (Jun. 1990). "Antisense Oligonucleotides: A New Therapeutic Principle," Chemical Reviews 90(4):543-584.

Authier F. et al. (1998) "Uptake and Metabolic Fate of [$His^{A8}$, $His^{B4}$, $Glu^{B10}$,$His^{B27}$] Insulin in Rat Liver In Vivo," Biochem J. 332;421-30.

Duckworth, W.C. et al. (Oct. 1998). "Insulin Degredation: Process and Potential," Endocr Rev. 19(5):608-24.

Senshang Lin, et al., "Comparative Pharmacokinetic and Pharmacodynamic Studies of Human Insulin and Analogues in Chronic Diabetic Yucatan Minipigs", The Journal of Pharmacology and Experimental Therapeutics, Apr. 13, 1998, pp. 959-966, vol. 286, No. 2.

Ribel et al., "Equivalent In Vivo Biological Activity of Insulin Analogues and Human Insulin Despite Different In Vitro Potencies," Diabetes, vol. 39, Sep. 1990, pp. 1033-1039. (7 pages total).

(56) References Cited

OTHER PUBLICATIONS

Valera, M. M. et al. (Dec. 2003). "Insulin Clearance in Obesity," J Am Coll Ntur. 22(6):487-93, Abstract Only.
Chilean Patent Office, Communication dated Jul. 13, 2017 by the Chilean Patent Office in counterpart Chilean Patent Application No. 201601844.
Chu et al., "The A14 Position of Insulin Tolerates Considerable Structural Alterations with Modest Effects on the Biological Behavior of the Hormone", Journal of Protein Chemistry, vol. 11, No. 5, 1992, pp. 571-577.
European Patent Office, Communication dated Sep. 20, 2017 by the European Patent Office in counterpart European Patent Application No. EP 15 73 7856.3.
European Patent Office; Communication dated May 10, 2017, in counterpart European application No. 14757629.2.
Chen et al., "Four New Monomeric Insulins Obtained by Alanine Scanning the Dimer-Forming Surface of the Insulin Molecule," Protein Eng'g 13:779-782 (2000).
Nakagawa et al., "Chiral Mutagenesis of Insulin, Contribution of the B20-B23 β-turn to Activity and Stability," J. Biol. Chem. 281:22386-22396, (2006).
Mohan. "Which Insulin to Use? Human or Animal?," Curr. Sci, 83:1544-1547 (2002).
United States Patent and Trademark Office communication dated Jan. 17, 2017 in counterpart U.S. Appl. No. 14/769,495.
European Patent Office; Communication dated Nov. 30, 2016, in counterpart European Application No. 14757629.2.
Colombian Patent Office; Communication dated Nov. 8, 2016, in counterpart Colombian application No. 15227010.
Kristensen et al., "Alanine Scanning Mutagenesis of Insulin," The Journal of Biological Chemistry, vol. 272, No. 20, 1997, pp. 12978-12983. (7 pages total).
Chile Patent Office; Communication dated Aug. 22, 2016, issued in corresponding Application No. 2015-002330.
Saudi Arabian Patent Office; Communication dated Apr. 30, 2016, issued in corresponding Application No. 515360933.
R. Vigneri, et al., "Insulin and its analogs: actions via insulin and IGF receptors", Acta Diabetol, 2010, pp. 271-278, vol. 47, No. 4.
NCBI, "insulin preproprotein [*Homo sapiens*]", NCBI Reference Sequence: NP_000198.1, Feb. 17, 2013, [online]<http://www.ncbi.nlm.nih.gov/protein/45576717sat=17&satkey=22757282> retrieved on Mar. 31, 2014.
Brange et al., "Monomeric Insulins and Their Experimental and Clinical Implications," Diabetes Care, vol. 13, No. 9, Sep. 1990, pp. 923-954. (32 pages total).
International Searching Authority, International Search Report for PCT/KR2014/001593 dated May 22, 2014.
International Searching Authority, Written Opinion of the International Search Authority for PCT/KR2014/001593 dated May 22, 2014.
Martin Lorenz et al., "Recent progress and future options in the development of GLP-1 receptor agonists for the treatment of diabesity", Bioorganic & Medicinal Chemistry Letters, 2013, pp. 4011-4018, vol. 23, No. 14.
International Searching Authority, International Search Report of PCT/KR2015/005455 dated Aug. 24, 2015 [PCT/ISA/210].
International Searching Authority, Written Opinion of PCT/KR2015/005455 dated Aug. 24, 2015 [PCT/ISA/237].
Colombian Patent Office; Communication dated Aug. 24, 2017, in counterpart Colombian application No. 15227010.
Taiwanese Intellectual Property Office; Communication dated Sep. 11, 2017 in counterpart application No. 103106674.
United States Patent and Trademark Office communication dated Jul. 19, 2017 in counterpart U.S. Appl. No. 14/769,495.
United States Patent and Trademark Office; Non-Final Rejection dated Apr. 17, 2018 in co-pending U.S. Appl. No. 15/315,020.
Japanese Patent Office; Communication dated Jan. 16, 2018 in counterpart Japanese application No. 2015-559199.
United States Patent and Trademark Office; Notice of Allowance dated Feb. 26, 2018 in U.S. Appl. No. 15/250,459.
United States Patent and Trademark Office; Non-Final Rejection dated Jan. 16, 2018 in U.S. Appl. No. 15/113,027.
United States Patent and Trademark Office; Non-Final Rejection dated Apr. 5, 2018 in U.S. Appl. No. 14/769,495.
Intellectual Property Office of Singapore; Communication dated Jan. 26, 2018 in counterpart Singaporean application No. 11201609872Y.
Chinese Patent and Trademark Office; communication dated Mar. 1, 2018, in Chinese Patent Application No. 201480006998.4.
Colombian Patent and Trademark Office; communication dated Feb. 16, 2018, in counterpart Colombian application No. NC2016/0004794.
Chilean Patent Office; Communication dated May 29, 2018 issued in counterpart Chilean Application No. 201603069.
Unirted States Patent and Trademark Office; Final Rejection dated Jul. 17, 2018 in co-pending U.S. Appl. No. 15/113,027.

* cited by examiner (a) Vehicle (b) Long acting insulin derivative conjugate 8.8nmol/kg (c) Long acting CA exendin-4 conjugate 0.36nmol/kg (d) Long acting insulin derivative conjugate 2.2nmol/kg + Long acting CA exendin-4 conjugate 0.36nmol/kg (e) Long acting insulin derivative conjugate 8.8nmol/kg + Long acting CA exendin-4 conjugate 0.36nmol/kg

SEQUENCE LISTING

```
<160> NUMBER OF SEQ ID NOS: 41

<210> SEQ ID NO 1
<211> LENGTH: 39
<212> TYPE: DNA
<213> ORGANISM: Artificial Sequence
<220> FEATURE:
<223> OTHER INFORMATION: Primer

<400> SEQUENCE: 1

gggtccctgc agaagcgtgc gattgtggaa caatgctgt                            39


<210> SEQ ID NO 2
<211> LENGTH: 39
<212> TYPE: DNA
<213> ORGANISM: Artificial Sequence
<220> FEATURE:
<223> OTHER INFORMATION: Primer

<400> SEQUENCE: 2

acagcattgt tccacaatcg cacgcttctg cagggaccc                            39


<210> SEQ ID NO 3
<211> LENGTH: 39
<212> TYPE: DNA
<213> ORGANISM: Artificial Sequence
<220> FEATURE:
<223> OTHER INFORMATION: Primer

<400> SEQUENCE: 3

tccctgcaga agcgtggcgc ggtggaacaa tgctgtacc                            39


<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4

ggtacagcat tgttccaccg cgccacgctt ctgcaggga                            39


<210> SEQ ID NO 5
<211> LENGTH: 36
<212> TYPE: DNA
<213> ORGANISM: Artificial Sequence
<220> FEATURE:
<223> OTHER INFORMATION: Primer

<400> SEQUENCE: 5

ctctaccagc tggaaaacgc gtgtaactga ggatcc                               36
```

<210> SEQ ID NO 6
<211> LENGTH: 36
<212> TYPE: DNA
<213> ORGANISM: Artificial Sequence
<220> FEATURE:
<223> OTHER INFORMATION: Primer

<400> SEQUENCE: 6
ggatcctcag ttacacgcgt tttccagctg gtagag 36

<210> SEQ ID NO 7
<211> LENGTH: 39
<212> TYPE: DNA
<213> ORGANISM: Artificial Sequence
<220> FEATURE:
<223> OTHER INFORMATION: Primer

<400> SEQUENCE: 7
gttaaccaac acttgtgtgc gtcacacctg gtggaagct 39

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
agcttccacc aggtgtgacg cacacaagtg ttggttaac 39

<210> SEQ ID NO 9
<211> LENGTH: 39
<212> TYPE: DNA
<213> ORGANISM: Artificial Sequence
<220> FEATURE:
<223> OTHER INFORMATION: Primer

<400> SEQUENCE: 9
ctagtgtgcg gggaacgagc gttcttctac acacccaag 39

<210> SEQ ID NO 10
<211> LENGTH: 39
<212> TYPE: DNA
<213> ORGANISM: Artificial Sequence
<220> FEATURE:
<223> OTHER INFORMATION: Primer

<400> SEQUENCE: 10
cttgggtgtg tagaagaacg ctcgttcccc gcacactag 39

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
gtgtgcgggg aacgaggcgc gttctacaca cccaagacc 39

<210> SEQ ID NO 12
<211> LENGTH: 39
<212> TYPE: DNA
<213> ORGANISM: Artificial Sequence
<220> FEATURE:

-continued

<223> OTHER INFORMATION: Primer

<400> SEQUENCE: 12
ggtcttgggt gtgtagaacg cgcctcgttc cccgcacac 39

<210> SEQ ID NO 13
<211> LENGTH: 39
<212> TYPE: DNA
<213> ORGANISM: Artificial Sequence
<220> FEATURE:
<223> OTHER INFORMATION: Primer

<400> SEQUENCE: 13
tgcggggaac gaggcttcgc gtacacaccc aagacccgc 39

<210> SEQ ID NO 14
<211> LENGTH: 39
<212> TYPE: DNA
<213> ORGANISM: Artificial Sequence
<220> FEATURE:
<223> OTHER INFORMATION: Primer

<400> SEQUENCE: 14
gcgggtcttg ggtgtgtacg cgaagcctcg ttccccgca 39

<210> SEQ ID NO 15
<211> LENGTH: 37
<212> TYPE: DNA
<213> ORGANISM: Artificial Sequence
<220> FEATURE:
<223> OTHER INFORMATION: Primer

<400> SEQUENCE: 15
ccagcatctg ctccctcgaa cagctggaga actactg 37

<210> SEQ ID NO 16
<211> LENGTH: 37
<212> TYPE: DNA
<213> ORGANISM: Artificial Sequence
<220> FEATURE:
<223> OTHER INFORMATION: Primer

<400> SEQUENCE: 16
cagtagttct ccagctgttc gagggagcag atgctgg 37

<210> SEQ ID NO 17
<211> LENGTH: 34
<212> TYPE: DNA
<213> ORGANISM: Artificial Sequence
<220> FEATURE:
<223> OTHER INFORMATION: Primer

<400> SEQUENCE: 17
cagcatctgc tccctcaacc agctggagaa ctac 34

<210> SEQ ID NO 18
<211> LENGTH: 34
<212> TYPE: DNA
<213> ORGANISM: Artificial Sequence
<220> FEATURE:
<223> OTHER INFORMATION: Primer

<400> SEQUENCE: 18
gtagttctcc agctggttga gggagcagat gctg 34

```
<210> SEQ ID NO 19
<211> LENGTH: 258
<212> TYPE: DNA
<213> ORGANISM: Artificial Sequence
<220> FEATURE:
<223> OTHER INFORMATION: Analog 1

<400> SEQUENCE: 19

ttcgttaacc aacacttgtg tggctcacac ctggtggaag ctctctacct agtgtgcggg     60

gaacgaggct tcttctacac acccaagacc cgccgggagg cagaggacct gcaggtgggg    120

caggtggagc tgggcggggg ccctggtgca ggcagcctgc agcccttggc cctggagggg    180

tccctgcaga agcgtgcgat tgtggaacaa tgctgtacca gcatctgctc cctctaccag    240

ctggagaact actgcaac                                                   258


<210> SEQ ID NO 20
<211> LENGTH: 86
<212> TYPE: PRT
<213> ORGANISM: Artificial Sequence
<220> FEATURE:
<223> OTHER INFORMATION: Analog 1

<400> SEQUENCE: 20

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Ala Ile Val Glu Gln Cys Cys Thr Ser Ile Cys Ser Leu Tyr Gln
65                  70                  75                  80

Leu Glu Asn Tyr Cys Asn
                85


<210> SEQ ID NO 21
<211> LENGTH: 258
<212> TYPE: DNA
<213> ORGANISM: Artificial Sequence
<220> FEATURE:
<223> OTHER INFORMATION: Analog 2

<400> SEQUENCE: 21

ttcgttaacc aacacttgtg tggctcacac ctggtggaag ctctctacct agtgtgcggg     60

gaacgaggct tcttctacac acccaagacc cgccgggagg cagaggacct gcaggtgggg    120

caggtggagc tgggcggggg ccctggtgca ggcagcctgc agcccttggc cctggagggg    180

tccctgcaga agcgtggcgc ggtggaacaa tgctgtacca gcatctgctc cctctaccag    240

ctggagaact actgcaac                                                   258


<210> SEQ ID NO 22
<211> LENGTH: 86
<212> TYPE: PRT
<213> ORGANISM: Artificial Sequence
<220> FEATURE:
<223> OTHER INFORMATION: Analog 2

<400> SEQUENCE: 22

Phe Val Asn Gln His Leu Cys Gly Ser His Leu Val Glu Ala Leu Tyr
 1               5                  10                  15
```

```
Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ala Val Glu Gln Cys Cys Thr Ser Ile Cys Ser Leu Tyr Gln
65                  70                  75                  80

Leu Glu Asn Tyr Cys Asn
                85


<210> SEQ ID NO 23
<211> LENGTH: 258
<212> TYPE: DNA
<213> ORGANISM: Artificial Sequence
<220> FEATURE:
<223> OTHER INFORMATION: Analog 3

<400> SEQUENCE: 23

ttcgttaacc aacacttgtg tggctcacac ctggtggaag ctctctacct agtgtgcggg     60

gaacgaggct tcttctacac acccaagacc cgccgggagg cagaggacct gcaggtgggg    120

caggtggagc tgggcggggg ccctggtgca ggcagcctgc agcccttggc cctggagggg    180

tccctgcaga agcgtggcat tgtggaacaa tgctgtacca gcatctgctc cctctaccag    240

ctggagaacg cgtgcaac                                                  258


<210> SEQ ID NO 24
<211> LENGTH: 86
<212> TYPE: PRT
<213> ORGANISM: Artificial Sequence
<220> FEATURE:
<223> OTHER INFORMATION: Analog 3

<400> SEQUENCE: 24

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Ala Cys Asn
                85


<210> SEQ ID NO 25
<211> LENGTH: 258
<212> TYPE: DNA
<213> ORGANISM: Artificial Sequence
<220> FEATURE:
<223> OTHER INFORMATION: Analog 4

<400> SEQUENCE: 25

ttcgttaacc aacacttgtg tgcgtcacac ctggtggaag ctctctacct agtgtgcggg     60

gaacgaggct tcttctacac acccaagacc cgccgggagg cagaggacct gcaggtgggg    120

caggtggagc tgggcggggg ccctggtgca ggcagcctgc agcccttggc cctggagggg    180
```

tccctgcaga agcgtggcat tgtggaacaa tgctgtacca gcatctgctc cctctaccag 240
ctggagaact actgcaac 258

<210> SEQ ID NO 26
<211> LENGTH: 86
<212> TYPE: PRT
<213> ORGANISM: Artificial Sequence
<220> FEATURE:
<223> OTHER INFORMATION: Analog 4

<400> SEQUENCE: 26

Phe Val Asn Gln His Leu Cys Ala Ser His Leu Val Glu Ala Leu Tyr
1 5 10 15

Leu Val Cys Gly Glu Arg Gly Phe Phe Tyr Thr Pro Lys Thr Arg Arg
20 25 30

Glu Ala Glu Asp Leu Gln Val Gly Gln Val Glu Leu Gly Gly Gly Pro
35 40 45

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

Leu Glu Asn Tyr Cys Asn
85

<210> SEQ ID NO 27
<211> LENGTH: 258
<212> TYPE: DNA
<213> ORGANISM: Artificial Sequence
<220> FEATURE:
<223> OTHER INFORMATION: Analog 5

<400> SEQUENCE: 27
ttcgttaacc aacacttgtg tggctcacac ctggtggaag ctctctacct agtgtgcggg 60
gaacgagcgt tcttctacac acccaagacc cgccgggagg cagaggacct gcaggtgggg 120
caggtggagc tgggcggggg ccctggtgca ggcagcctgc agcccttggc cctggagggg 180
tccctgcaga agcgtggcat tgtggaacaa tgctgtacca gcatctgctc cctctaccag 240
ctggagaact actgcaac 258

<210> SEQ ID NO 28
<211> LENGTH: 86
<212> TYPE: PRT
<213> ORGANISM: Artificial Sequence
<220> FEATURE:
<223> OTHER INFORMATION: Analog 5

<400> SEQUENCE: 28

Phe Val Asn Gln His Leu Cys Gly Ser His Leu Val Glu Ala Leu Tyr
1 5 10 15

Leu Val Cys Gly Glu Arg Ala Phe Phe Tyr Thr Pro Lys Thr Arg Arg
20 25 30

Glu Ala Glu Asp Leu Gln Val Gly Gln Val Glu Leu Gly Gly Gly Pro
35 40 45

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

Leu Glu Asn Tyr Cys Asn

85

<210> SEQ ID NO 29
<211> LENGTH: 258
<212> TYPE: DNA
<213> ORGANISM: Artificial Sequence
<220> FEATURE:
<223> OTHER INFORMATION: Analog 6

<400> SEQUENCE: 29
ttcgttaacc aacacttgtg tggctcacac ctggtggaag ctctctacct agtgtgcggg 60
gaacgaggcg cgttctacac acccaagacc cgccgggagg cagaggacct gcaggtgggg 120
caggtggagc tgggcggggg ccctggtgca ggcagcctgc agcccttggc cctggagggg 180
tccctgcaga agcgtggcat tgtggaacaa tgctgtacca gcatctgctc cctctaccag 240
ctggagaact actgcaac 258

<210> SEQ ID NO 30
<211> LENGTH: 86
<212> TYPE: PRT
<213> ORGANISM: Artificial Sequence
<220> FEATURE:
<223> OTHER INFORMATION: Analog 6

<400> SEQUENCE: 30

Phe Val Asn Gln His Leu Cys Gly Ser His Leu Val Glu Ala Leu Tyr
1 5 10 15

Leu Val Cys Gly Glu Arg Gly Ala Phe Tyr Thr Pro Lys Thr Arg Arg
20 25 30

Glu Ala Glu Asp Leu Gln Val Gly Gln Val Glu Leu Gly Gly Gly Pro
35 40 45

Gly Ala Gly Ser Leu Gln Pro Leu Ala Leu Glu Gly Ser Leu Gln Lys
50 55 60

Arg Gly Ile Val Glu Gln Cys Cys Thr Ser Ile Cys Ser Leu Tyr Gln
65 70 75 80

Leu Glu Asn Tyr Cys Asn
85

<210> SEQ ID NO 31
<211> LENGTH: 258
<212> TYPE: DNA
<213> ORGANISM: Artificial Sequence
<220> FEATURE:
<223> OTHER INFORMATION: Analog 7

<400> SEQUENCE: 31
ttcgttaacc aacacttgtg tggctcacac ctggtggaag ctctctacct agtgtgcggg 60
gaacgaggct tcgcgtacac acccaagacc cgccgggagg cagaggacct gcaggtgggg 120
caggtggagc tgggcggggg ccctggtgca ggcagcctgc agcccttggc cctggagggg 180
tccctgcaga agcgtggcat tgtggaacaa tgctgtacca gcatctgctc cctctaccag 240
ctggagaact actgcaac 258

<210> SEQ ID NO 32
<211> LENGTH: 86
<212> TYPE: PRT
<213> ORGANISM: Artificial Sequence
<220> FEATURE:
<223> OTHER INFORMATION: Analog 7

<400> SEQUENCE: 32

```
Phe Val Asn Gln His Leu Cys Gly Ser His Leu Val Glu Ala Leu Tyr
 1               5                  10                  15

Leu Val Cys Gly Glu Arg Gly Phe Ala Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85


<210> SEQ ID NO 33
<211> LENGTH: 261
<212> TYPE: DNA
<213> ORGANISM: Artificial Sequence
<220> FEATURE:
<223> OTHER INFORMATION: Analog 8

<400> SEQUENCE: 33

ttcgttaacc aacacttgtg tggctcacac ctggtggaag ctctctacct agtgtgcggg      60

gaacgaggct tcttctacac acccaagacc cgccgggagg cagaggacct gcaggtgggg     120

caggtggagc tgggcggggg ccctggtgca ggcagcctgc agcccttggc cctggagggg     180

tccctgcaga agcgtggcat tgtggaacaa tgctgtacca gcatctgctc cctcgaacag     240

ctggagaact actgcaactg a                                               261


<210> SEQ ID NO 34
<211> LENGTH: 86
<212> TYPE: PRT
<213> ORGANISM: Artificial Sequence
<220> FEATURE:
<223> OTHER INFORMATION: Analog 8

<400> SEQUENCE: 34

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Glu Gln
65                  70                  75                  80

Leu Glu Asn Tyr Cys Asn
                85


<210> SEQ ID NO 35
<211> LENGTH: 261
<212> TYPE: DNA
<213> ORGANISM: Artificial Sequence
<220> FEATURE:
<223> OTHER INFORMATION: Analog 9

<400> SEQUENCE: 35

ttcgttaacc aacacttgtg tggctcacac ctggtggaag ctctctacct agtgtgcggg      60
```

-continued

```
gaacgaggct tcttctacac acccaagacc cgccgggagg cagaggacct gcaggtgggg    120

caggtggagc tgggcggggg ccctggtgca ggcagcctgc agcccttggc cctggagggg    180

tccctgcaga agcgtggcat tgtggaacaa tgctgtacca gcatctgctc cctcaaccag    240

ctggagaact actgcaactg a                                              261


<210> SEQ ID NO 36
<211> LENGTH: 86
<212> TYPE: PRT
<213> ORGANISM: Artificial Sequence
<220> FEATURE:
<223> OTHER INFORMATION: Analog 9

<400> SEQUENCE: 36

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Asn Gln
65                  70                  75                  80

Leu Glu Asn Tyr Cys Asn
                85


<210> SEQ ID NO 37
<211> LENGTH: 21
<212> TYPE: PRT
<213> ORGANISM: Artificial Sequence
<220> FEATURE:
<223> OTHER INFORMATION: A chain of insulin

<400> SEQUENCE: 37

Gly Ile Val Glu Gln Cys Cys Thr Ser Ile Cys Ser Leu Tyr Gln Leu
 1               5                  10                  15

Glu Asn Tyr Cys Asn
            20


<210> SEQ ID NO 38
<211> LENGTH: 30
<212> TYPE: PRT
<213> ORGANISM: Artificial Sequence
<220> FEATURE:
<223> OTHER INFORMATION: B chain of insulin

<400> SEQUENCE: 38

Phe Val Asn Gln His Leu Cys Gly Ser His Leu Val Glu Ala Leu Tyr
 1               5                  10                  15

Leu Val Cys Gly Glu Arg Gly Phe Phe Tyr Thr Pro Lys Thr
            20                  25                  30


<210> SEQ ID NO 39
<211> LENGTH: 31
<212> TYPE: PRT
<213> ORGANISM: Artificial Sequence
<220> FEATURE:
<223> OTHER INFORMATION: GLP-1(7-37)

<400> SEQUENCE: 39

His Ala Glu Gly Thr Phe Thr Ser Asp Val Ser Ser Tyr Leu Glu Gly
```

-continued

```
 1               5                  10                  15

Gln Ala Ala Lys Glu Phe Ile Ala Trp Leu Val Lys Gly Arg Gly
            20                  25                  30


<210> SEQ ID NO 40
<211> LENGTH: 39
<212> TYPE: PRT
<213> ORGANISM: Artificial Sequence
<220> FEATURE:
<223> OTHER INFORMATION: exendin-3

<400> SEQUENCE: 40

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35


<210> SEQ ID NO 41
<211> LENGTH: 39
<212> TYPE: PRT
<213> ORGANISM: Artificial Sequence
<220> FEATURE:
<223> OTHER INFORMATION: exendin-4

<400> SEQUENCE: 41

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

METHOD FOR TREATING DIABETES COMPRISING LONG-ACTING INSULIN ANALOGUE CONJUGATE AND LONG-ACTING INSULINOTROPIC PEPTIDE CONJUGATE

CROSS REFERENCE TO RELATED APPLICATIONS

This application is a National Phase application under 35 U.S.C. § 371 of International Application No. PCT/KR2015/005424 filed May 29, 2015, which claims priority benefit to KR Application No. 10-2014-0065072 filed May 29, 2014, the disclosures of each of which are herein incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 768502000300SEQLIST.txt, date recorded: Nov. 21, 2016, size: 17 KB).

TECHNICAL FIELD

The present invention relates to a composition for the prevention or treatment of diabetes including a long-acting insulin conjugate and a long-acting insulinotropic peptide conjugate, and a method for treating diabetes including the step of administering the composition.

In addition, the present invention relates to a pharmaceutical composition for reducing side effects of pancreatic beta cells in diabetic patients, including a long-acting insulin analogue conjugate and a long-acting insulinotropic peptide conjugate, and to a method for reducing side effects of pancreatic beta cells in diabetic patients, including the step of administering the composition. Specifically, the present invention is characterized in reducing side effects such as abnormality in pancreatic beta cell function associated with the development of diabetes, a reduction in pancreatic beta cells, and a lipotoxicity or glucotoxicity.

BACKGROUND ART

Insulin is a peptide secreted by the beta cells of the pancreas, and plays an important role in controlling the blood glucose level in the body. A metabolic disease associated with an elevated blood glucose level due to lack of insulin secretion or an abnormality in the function of insulin is called diabetes. When the elevated blood glucose level is due to the failure in insulin secretion by the pancreas it is called type 1 diabetes, whereas the elevated blood glucose level is due to the abnormality in insulin secretion or abnormal function of the secreted insulin in the body it is called type 2 diabetes. Patients with type 2 diabetes are usually treated with an oral hypoglycemic agent having a chemical substance as a main ingredient, and in some cases, given with insulin, whereas patients with type 1 diabetes essentially require insulin treatment.

The most common insulin therapy currently available is an insulin injection before and/or after meals. Currently, injectable insulin is available on the market, and in principle, is given in a subcutaneous injection. The method of administration varies depending on its time course of action. Insulin injection shows a more rapid hypoglycemic effect than oral administration, and can be safely used when oral administration is not possible. Also, there is no dose limit for insulin use. However, long-term use of insulin three times a day can lead to disadvantages such as aversion to needles, difficulty in handling the injection device, hypoglycemia, and weight gain due to long-term use of insulin. Weight gain may increase the risk of cardiovascular disease and a side effect of insulin resistance. Meanwhile, there have been many efforts to maximize the efficacy by maintaining the long term, elevated levels of insulin peptide drugs after absorption by the body. For example, long-acting insulin formulations such as Lantus (Insulin glargine; Sanofi Aventis) and Levemir (Insulin detemir; Novo Nordisk) have been developed and are commercially available. Unlike insulin NPH (Neutral Protamine Hagedorn), these long-acting drugs reduce the risk of hypoglycemia during sleep, and in particular, Levemir was associated with somewhat less weight gain. However, these drug formulations are also disadvantageous in that they must be given once or twice a day.

Meanwhile, one insulinotropic peptide, glucagon like peptide-1 (GLP-1), is an incretin hormone secreted by L-cells of the ileum and colon. Glucagon like peptide-1 functions to augment insulin release and induces glucose dependent secretion so as to prevent hypoglycemic episodes. Owing to this property, it received attention as a potential treatment for type 2 diabetes. However, the primary obstacle to the use of GLP-1 as a therapeutic agent is its extremely short half-life of less than 2 minutes in blood. Currently, exendin-4 is commercially available as a glucagon like peptide-1 receptor agonist, and it is a glucagon like peptide-1 analogue purified from the salivary gland of a gila monster. Exendin-4 has resistance to only DPP IV (Dipeptidyl peptidase-4), and higher physiological activity than glucagon like peptide-1. As a result, it had an in vivo half-life of 2 to 4 hours, which is longer than that of glucagon like peptide-1 (U.S. Pat. No. 5,424,286). However, with the method for increasing the resistance to only DPP IV, it cannot be expected to sustain a sufficient physiological activity, and for example, in the case of commercially available exendin-4 (exenatide), there still remains a problem that it must be administered to a patient twice a day, and the administration causes adverse events such as vomiting and nausea which are a significant burden on the patient.

These diabetes-related diseases, although there is a difference in time, generally induce a reduction in the pancreatic beta cell mass due to a function loss and apoptosis of pancreatic beta cells.

When blood glucose levels increase continuously, the pancreatic beta cells increase insulin secretion based on enhancement of the function thereof and an increase in the beta cell mass in order to maintain in-vivo blood glucose levels, but such secretion-increasing action is limited. That is, if the amount of insulin required to maintain in-vivo blood glucose levels normally is more than that of insulin capable of being produced by pancreatic beta cells, and as a result blood glucose levels are ultimately increased and so the progression of type 2 diabetes becomes serious.

Clinically, type 2 diabetes progresses in the order of an insulin resistance, a decrease in insulin secretion, and an abnormality in the function of pancreatic beta cells and a reduction in the pancreatic beta cell mass. In particular, the abnormality in the function of the beta cells and the reduction in pancreatic beta cell mass is facilitated by increased blood lipid and glucose. The concentration of such blood lipid and glucose will induce lipotoxicity and/or glucotoxicity and so weaken both the function of beta cells as well as the actions of insulin, and will ultimately worsen the prognosis of type 2 diabetes. Accordingly, inhibition of the lipotoxicity and glucotoxicity can significantly mitigate the progression of type 2 diabetes through the retention of the beta cell function and mass as well as through the improvement of insulin resistance.

Insulin is a peptide secreted from the beta cells of the pancreas, and plays a role in controlling blood glucose levels in the body. Accordingly, an abnormality in the function of insulin and a reduction in the beta cell mass are closely associated with an increase in blood glucose levels due to a reduction in the amount of insulin in the body. Thus, diabetic patients with decreased insulin secretion may be treated using an extrinsic insulin. According to previous studies, it is known that administration of the extrinsic insulin not only exhibits excellent effects in improving blood glucose levels, but also inhibits occurrence of stress due to excessive insulin secretion of pancreatic beta cells.

However, administration of the extrinsic insulin has a major drawback of inducing a weight gain, and such weight gain involves an increase in blood lipid levels. Accordingly, it is likely to worsen the progenesis of the diabetes.

Glucagon-like peptide-1 (GLP-1) receptor agonist, a kind of insulinotropic peptide including exendin-4, is known to have the effects of controlling blood glucose levels and reducing the body weight in type 2 diabetes patients. Moreover, the GLP-1 receptor agonist can increase the beta cell mass by controlling the neogenesis, proliferation, and differentation of the beta cells as well as the apopotosis of the beta cells.

Actually, in a type 2 diabetes-induced rodent model, it was confirmed that administration of GLP-1 or exendin-4 stimulates the growth and differentiation of the beta cells, thus increasing the beta cell mass. However, the GLP-1 receptor agonist continuously stimulates the insulin secretion in pancreatic beta cells and thus involves the possibility of malfunction degraded due to an increase in the beta cell stress.

In order to solve the above problems, the present inventors suggested a long-acting protein conjugatein which a physiologically active polypeptide is linked to an immunoglobulin Fc region via a non-peptidyl polymer as a linker by a covalent bond, thereby sustaining the activity and improving the stability of the protein drug at the same time (Korean Patent No. 10-0725315). In particular, they found that each of the long-acting insulin conjugate and the long-acting exendin-4 conjugate exerts remarkably increased in vivo efficacy (Korean Patent Nos. 10-1058209 and 10-1330868).

However, there are still the problems of weight gain, or vomiting and nausea, when insulin or exendin-4 is injected in an amount which maintains a stable blood glucose level. Thus, there is an urgent need to develop a therapeutic method showing excellent therapeutic effects on diabetes with lower doses and less frequent use of the drug. In addition, such studies were focused on increasing in in-vivo half life of the physiologically active polypeptide, and studies on a method capable of reversing a function loss of the pancreatic beta cells and/or a reduction in the pancreatic beta cell mass due to an apoptosis of the pancreatic beta cells, which is a side effect that causes a poor prognosis of diabetes in patients are incomplete.

DISCLOSURE

Technical Problem

The present inventors have made many studies and experiments to develop a therapeutic agent for diabetes which has the long-lasting therapeutic efficacy and lowers adverse events such as vomiting and nausea at the same time, and a therapeutic agent for diabetes, which can maintain and increase a pancreatic beta cell function and the cell mass, and provide safety from the potential beta cell stress. They attempted to perform combination administration of a long-acting exendin-4 conjugate and a long-acting insulin analogue conjugate that stimulate a glucagon like peptide-1 receptor and an insulin receptor at the same time. As a result, they found that combination administration of the long-acting insulin analogue conjugate and the long-acting exendin-4 conjugate improves in vivo duration of efficacy and stability, and remarkably reduces the doses of the two drugs, leading to a stable blood glucose level. They also found that it improves the adverse events such as vomiting and nausea induced by glucagon like peptide-1 agonist and exendin-4 or derivatives thereof and the use of long-acting exendin-4 conjugate reduces weight gain caused by the use of insulin. Further, they found that it can significantly reduce lipotoxicity and glucotoxicity, which are the main cause of decreased function and mass of the beta cells, and can alleviate the progression of diabetes. The present invention was completed based on these findings.

Technical Solution

An objective of the present invention is to provide a pharmaceutical composition for the prevention or treatment of diabetes, including a long-acting insulin analogue conjugate and a long-acting insulinotropic peptide conjugate.

Another objective of the present invention is to provide a method for preventing or treating diabetes, including administering the composition to a subject having diabetes or at risk of having diabetes.

Still another objective of the present invention is to provide a pharmaceutical composition for reducing one or more pancreatic beta cell side-effects selected from the group consisting of lipotoxicity, glucotoxicity, abnormality in the function of pancreatic beta cells and a reduction in pancreatic beta cells in diabetic patients, including a long-acting insulin analogue conjugate and a long-acting insulinotropic peptide conjugate.

Still another objective of the present invention is to provide a method for reducing one or more pancreatic beta cell side-effects selected from the group consisting of lipotoxicity, glucotoxicity, abnormality in the function of pancreatic beta cells and reduction in pancreatic beta cell mass in a diabetic subject, including a step of administering the composition to the subject suffering from diabetes or at risk of having diabetes.

Advantageous Effects

A long-acting insulin analogue conjugate and a long-acting exendin-4 conjugate of the present invention show excellent therapeutic effects on diabetes, and in particular, the combination administration thereof stimulates an insulin receptor and a glucagon like peptide-1 receptor at the same time to improve in vivo duration of the efficacy and stability thereof, and to remarkably reduce the required doses of the drugs and stably control the blood glucose at a stable level, leading to improvements in hypoglycemia and weight gain. In addition, it inhibits vomiting and nausea and has improved drug compliance as a therapeutic agent for diabetes. In particular, it has remarkably improved stability in blood and in vivo duration of efficacy allowing a reduction in administration frequency, which contributes to patient convenience.

Furthermore, the long-acting insulin analogue conjugate and the long-acting insulinotropic peptide conjugate according to the present invention exhibit excellent diabetic treatment effects, especially when administered in combination, and stimulate insulin receptors and glucagon-like peptide-1 receptors simultaneously, thus enhancing in-vivo duration and stability, and further improve the function of beta cells and increase the mass thereof through the reduction of lipotoxicity and glucotoxicity, which are side-effects incurred due to the progression of diabetes. In addition, the present invention can provide a composition in which the disadvantages of the insulin preparation have been reduced by alleviating low blood glucose levels and weight gain.

BEST MODE

Figure 1:
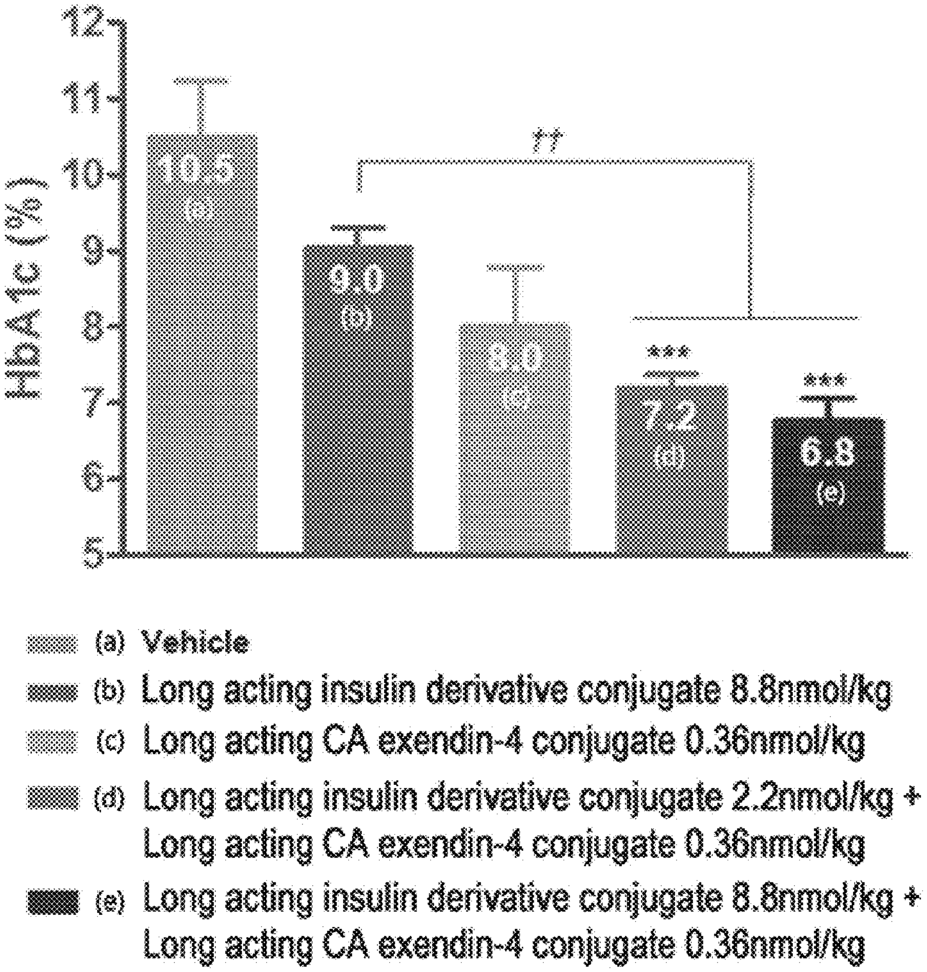
FIG. 1 is a graph showing glycosylated hemoglobin (HbA1c) levels, which are measured to examine blood glucose control by combination administration of a long-acting insulin analogue conjugate and a long-acting exendin-4 conjugate to db/db mice (*P<0.05, P<0.01, *P<0.001 by Dunnet's MC test, vs. vehicle) (†P<0.05, ††P<0.01, ††† P<0.001 by Dunnet's MC test, vs. single administration of long-acting insulin analogue conjugate).

In an aspect, the present invention provides a pharmaceutical composition for the prevention or treatment of diabetes, including a long-acting insulin analogue conjugate and a long-acting insulinotropic peptide conjugate which are similar in in vivo half-life. The composition of the present invention is characterized by combination administration of the long-acting insulin analogue conjugate and the long-acting insulinotropic peptide conjugate.

In detail, the composition may be a pharmaceutical composition for the prevention or treatment of diabetes, including the long-acting insulin analogue conjugate in which an insulin analogue is linked to a biocompatible material capable of prolonging duration of its activity via a linker or a covalent bond; and the long-acting insulinotropic peptide conjugate in which an insulinotropic peptide is linked to a biocompatible material capable of prolonging duration of its activity via a linker or a covalent bond.

In another aspect, the invention provides a pharmaceutical composition for reducing one or more pancreatic beta cell side-effects selected from the group consisting of lipotoxicity, glucotoxicity, abnormality in the function of pancreatic beta cells and a reduction in the pancreatic beta cell mass in diabetic patients, containing a long-acting insulin analogue conjugate and a long-acting insulinotropic peptide conjugate, which have similar in-vivo half life. The composition of the present invention is characterized in that a long-acting insulin analogue conjugate and a long-acting insulinotropic peptide conjugate are administered in combination.

Specifically, the composition of the present invention can be a pharmaceutical composition for reducing one or more pancreatic beta cell side-effects selected from the group consisting of lipotoxicity, glucotoxicity, an abnormality in the function of pancreatic beta cells and a reduction in the pancreatic beta cell mass in diabetic patients, containing:

a long-acting insulin analogue conjugate in which an insulin analogue is linked to biocompatible material capable of prolonging duration of activity of the insulin analogue via a linker or a covalent bond, and a long-acting insulinotropic peptide conjugate in which an insulinotropic peptide is linked to a biocompatible material capable of prolonging duration of activity of the insulinotropic peptide via a linker or a covalent bond.

The composition of the present invention can reduce lipotoxicity, glucotoxicity, abnormality in the function of pancreatic beta cells and reduction in the pancreatic beta cell mass at the same time.

Since insulinotropic peptides, such as insulin analogue and glucagon-like peptide-1, control blood glucose levels through different mechanisms of action, only studies for their use as therapeutic agents for controlling blood glucose levels have been performed based the finding that their efficacy can be maximized upon combination administration. However, there have been no studies verifying that the combination administration improves the function and mass of beta cells through the reduction and complementary action on lipotoxicity and glucotoxicity, thereby reducing the pancreatic beta cell side-effects, which can occur with single administration of insulin or insulinotropic peptide. The novel use as described above was first developed by the present inventors.

The composition of the present invention is characterized in that it can not only reduce the pancreatic beta cell side-effects, but also decrease the concentration of triglyceride in the blood to thereby reduce the lipid toxicity, control a blood glucose function to thereby reduce the glucotoxicity, and maintain and/or increase the pancreatic beta cell mass to thereby inhibit the progression of diabetes. Accordingly, the composition of the present invention can alleviate the progression of diabetes.

The above-described composition is characterized in that it improves the prognosis of diabetes in a diabetic subject to which it has been administered.

In the composition, a molar ratio of long-acting insulinotropic peptide conjugate:insulin analogue conjugate may be in the range of 1:0.01~1:50. Example of the insulinotropic peptide conjugate may be an exendin conjugate, but is not limited thereto.

Mode for Invention

As used herein, the term "long-acting insulin analogue conjugate" or "long-acting insulinotropic peptide conjugate"

refers to a conjugate in which the insulin analogue or the insulinotropic peptide is linked to a biocompatible material or a carrier via a covalent bond or a non-covalent bond, and formation of the conjugate prolongs duration of the activity of the corresponding insulin analogue or insulinotropic peptide, compared to non-conjugated analogue or insulinotropic peptide.

Administration of the long-acting insulin analogue conjugate reduces the required doses of the drugs and also alleviates adverse events such as weight gain, vomiting and nausea, compared to the native insulin.

In the present invention, the agent capable of increasing half-life and bioavailability of the insulin analogue and the insulinotropic peptide or sustaining their activity may be a carrier that directly binds to the insulin analogue and the insulinotropic peptide via a covalent bond, or it refers to an agent capable of increasing in vivo activity of the insulin analogue even though the covalent bond is not directly formed.

As used herein, the term "biocompatible material or carrier" is a material capable of prolonging duration of the activity of the insulin analogue or the insulinotropic peptide when it is linked to the corresponding analogue or peptide via a covalent or non-covalent bond to form a conjugate. For example, the material capable of prolonging in vivo half-life of the corresponding analogue or peptide by formation of the conjugate may be the biocompatible material or carrier according to the present invention. The biocompatible material capable of binding to the insulin analogue and the insulinotropic peptide may be exemplified by various biocompatible materials including polyethylene glycol, fatty acid, cholesterol, albumin and fragments thereof, albumin-binding materials, a polymer of repeating units of a particular amino acid sequence, an antibody, antibody fragments, FcRn binding material, connective tissues, nucleotides, fibronectin, transferrin, saccharides, or polymers, which forms a covalent or non-covalent bond to prolong in vivo half-life. Further, the linkage between the insulin analogue or the insulinotropic peptide and the biocompatible material capable of prolonging in vivo half-life includes genetic recombination and in vitro conjugation using a high- or low-molecular-weight compound, but is not limited to any linkage method. The FcRn binding material may be an immunoglobulin Fc region.

As used herein, the term "insulin analogue (or analog)" refers to a peptide having variant of one or more amino acids of a native sequence.

The insulin analogue may be an insulin analogue which has amino acid variant in B chain or A chain of insulin and has reduced insulin titer and/or reduced insulin receptor-binding affinity, compared to the native insulin. The amino acid sequence of the native insulin is as follows.

A chain:

(SEQ ID NO: 37)
Gly-Ile-Val-Glu-Gln-Cys-Cys-Thr-Ser-Ile-Cys-Ser-Leu-Tyr-Gln-Leu-Glu-Asn-Tyr-Cys-Asn

B chain:

(SEQ ID NO: 38)
Phe-Val-Asn-Gln-His-Leu-Cys-Gly-Ser-His-Leu-Val-Glu-Ala-Leu-Tyr-Leu-Val-Cys-Gly-Glu-Arg-Gly-Phe-Phe-Tyr-Thr-Pro-Lys-Thr

The insulin used in Examples of the present invention may be an insulin analogue produced by a genetic recombination technology, but the present invention is not limited thereto. The insulin includes all insulins having reduced in-vitro titer and/or reduced insulin receptor-binding affinity. Preferably, the insulin includes inverted insulin, insulin variants, insulin fragments, etc., and it may be prepared by a solid phase method as well as a genetic recombination method, but is not limited thereto.

The insulin analogue is a peptide that retains the function of controlling the blood glucose level in the body, which is equal to that of insulin, and such peptide includes insulin agonists, derivatives, fragments, variants, etc.

The insulin agonist of the present invention refers to a compound that binds to the insulin receptor to show the biological activity equal to that of insulin, which is irrelevant to the structure of insulin.

The insulin analogue of the present invention refers to a peptide having homology with respective amino acid sequences of A chain and B chain of the native insulin, which may have at least one amino acid residue changed by an alteration selected from the group consisting of substitution (e.g., alpha-methylation, alpha-hydroxylation), deletion (e.g., deamination), modification (e.g., N-methylation), and combinations thereof, and has a function of regulating the blood glucose level in the body.

In the present invention, the insulin analogue refers to a peptide mimic or a low- or high-molecular-weight compound that binds to the insulin receptor to regulate the blood glucose level, even though its amino acid sequence has no homology with that of the native insulin.

The insulin fragment of the present invention refers to a fragment having one or more amino acids added or deleted at insulin, in which the added amino acids may be non-naturally occurring amino acids (e.g., D-type amino acid), and this insulin fragment has a function of regulating the blood glucose level in the body.

The insulin variant of the present invention is a peptide having one or more amino acid sequences different from those of insulin, and it refers to a peptide that retains the function of regulating the blood glucose level in the body.

Each of the preparation methods for the insulin agonists, derivatives, fragments, and variants of the present invention may be used individually or in combination. For example, the present invention includes a peptide that has one or more different amino acids and deamination of the N-terminal amino acid residue, and has a function of regulating the blood glucose level in the body.

Specifically, the insulin analogue may be characterized in substitution of one or more amino acids selected from the group consisting of amino acids at positions 1, 2, 3, 5, 8, 10, 12, 16, 23, 24, 25, 26, 27, 28, 29, and 30 of B chain and at positions 1, 2, 5, 8, 10, 12, 14, 16, 17, 18, 19 and 21 of A chain with other amino acids, specifically alanine, glutamic acid, asparagine, isoleucine, valine, glutamine, glycine, lysine, histidine, cysteine, phenylalanine, tryptophan, proline, serine, threonine, aspartic acid. Further, an insulin analogue having deletion of one or more amino acids may be also included in the scope of the present invention, but there is no limitation in the insulin analogue.

The insulin analogue may be an insulin analogue having higher half-life than the native insulin, when it hinds with the biocompatible material or the carrier. The insulin analogue may be insulin analogues disclosed in Korean Patent Nos. 2014-0022909 and 2014-0006938, but is not limited thereto.

As used herein, the term "long-acting insulinotropic peptide conjugate" refers to an insulinotropic peptide linked with an immunoglobulin Fc region via a non-peptidyl linker.

As used herein, the term "insulinotropic peptide" refers to a peptide that retains the function of releasing insulin, and stimulates synthesis or expression of insulin in the beta cells of the pancreas. Specifically, the insulinotropic peptide is GLP (Glucagon like peptide)-1, exendin-3, or exendin-4, but is not limited thereto. The insulinotropic peptide includes native insulinotropic peptides, precursors thereof, agonists thereof, derivatives thereof, fragments thereof, and variants thereof.

The insulinotropic, peptide derivative of the present invention may include a desamino-histidyl derivative where the N-terminal amino group of insulinotropic peptide is deleted, beta-hydroxy imidazopropionyl-derivative where the amino group is substituted with a hydroxyl group, dimethyl-histidyl derivative where the amino group is modified with two methyl groups, beta-carboxyimidazopropionyl-derivative where the N-terminal amino group is substituted with a carboxyl group, or an imidazoacetyl-derivative where the alpha carbon of the N-terminal histidine residue is deleted to remain only the imidazoacetyl group and thus the positive charge of the amino group is removed, etc. Other N-terminal amino group-mutated derivatives are included within the scope of the present invention.

In the present invention, the insulinotropic peptide derivative may be an exendin-4 derivative having a chemically mutated N-terminal amino group or amino acid residue, even more specifically an exendin-4 derivative which is prepared by removing or substituting the alpha amino group present in the alpha carbon of the N-terminal His1 residue of exendin-4 or by removing or substituting the alpha carbon. Still more specifically, desamino-histidyl-exendin-4 (DA-Exendin-4) with removal of the N-terminal amino group, beta-hydroxy imidazopropyl-exendin-4 (HY-exendin-4) prepared by substitution with a hydroxyl group, beta-carboxy imidazopropyl-exendin-4 (CX-exendin-4) prepared by substitution with a carboxyl group, dimethyl-histidyl-exendin-4 (DM-exendin-4) prepared by modification with two methyl residues, or imidazoacetyl-exendin-4 (CA-exendin-4) with removal of alpha carbon of N-terminal histidine residue, but are not limited thereto.

GLP-1 is a hormone secreted by the small intestine, and usually promotes biosynthesis and secretion of insulin, inhibits glucagon secretion, and promotes glucose uptake by the cells. In the small intestine, a glucagon precursor is decomposed into three peptides, that is, glucagon, GLP-1, and GLP-2. Here, the GLP-1 refers to GLP-1 (1-37), which is originally in the form having no insulinotropic function, but is then processed and converted into one in the activated GLP-1 (7-37) forms. The sequence of the GLP-1 (7-37) amino acid is as follows:

```
GLP-1(7-37):
                                   (SEQ ID NO: 39)
HAEGT FTSDV SSYLE GQAAK EFIAW LVKGR G
```

The GLP-1 derivative refers to a peptide which exhibits an amino acid sequence homology of at least 80% with that of GLP-1, may be in the chemically modified form, and exhibits an insulinotropic function of at least equivalent to or higher than that of GLP-1.

The GLP-1 fragment refers to one in the form in which one or more amino acids are added or deleted at an N-terminus or a C-terminus of a native GLP-1, in which the added amino acid is possibly a non-naturally occurring amino acid (e.g., D-type amino acid).

The GLP-1 variant refers to a peptide possessing an insulinotropic function, which has one or more amino acid sequences different from those of a native GLP-1.

Exendin-3 and the exendin-4 are insulinotropic peptides consisting of 39 amino acids, which have a 53% amino acid sequence homology with GLP-1. The amino acid sequences of the exendin-3 and the exendin-4 are as follows:

```
Exendin-3:
                                            (SEQ ID NO: 40)
HSDGT FTSDL SKQME EEAVR LFIEW LKNGG PSSGA PPPS

Exendin-4:
                                            (SEQ ID NO: 41)
HGEGT FTSDL SKQME EEAVR LFIEW LKNGG PSSGA PPPS
```

The exendin agonist refers to a compound binding to exendin receptors in vivo and having biological activity equivalent to that of exendin, which is irrelevant to the structure of exendin, and the exendin derivative refers to a peptide having at least 80% amino acid sequence homology with the native exendin, which may have some groups on the amino acid residue chemically substituted (e.g., alpha-methylation, alpha-hydroxylation), deleted (e.g., deamination), or modified (e.g., N-methylation), and has an insulinotropic function.

The exendin fragment refers to a fragment having one or more amino acids added or deleted at the N-terminus or the C-terminus of the native exendin in which non-naturally naturally occurring amino acids (e.g., D-type amino acid) may be added, and has an insulinotropic function.

The exendin variant refers to a peptide having at least one amino acid sequence different from that of the native exendin, which has an insulinotropic function, and the exendin variant includes peptides in which lysine at position 12 of exendin-4 is substituted with serine or arginine.

Each of the preparation methods for the exendin agonists, derivatives, fragments, and variants may be used individually or in combination. For example, the present invention includes an insulinotropic peptide having an amino acid sequence having at least one different amino acid, and having the amino acid residue which is deaminated at the N-terminus:

In an exemplary embodiment, the native insulinotropic peptide and the modified insulinotropic peptide used in the present invention may be synthesized using a solid phase synthesis method, and most of the native peptides including a native insulinotropic peptide may be produced by a recombination technology.

The insulin analogue conjugate and the insulinotropic peptide conjugate may be represented by the following formula:

X—La—F wherein X is an insulin analogue or an insulinotropic peptide, in which the insulin analogue prepared by modification of one or more amino acids of B chain or A chain of insulin, L is a linker, a is 0 or a natural number (when a is 2 or higher, each L is independent), F is selected from polyethylene glycol, fatty acid, cholesterol, albumin and a fragment thereof, a particular amino acid sequence, an antibody and a fragment thereof, an FcRn binding material, fibronectin, saccharide, etc.

The immunoglobulin Fc region is safe for use as a drug carrier because it is a biodegradable polypeptide that is metabolized in the body. Also, the immunoglobulin Fe region has a relatively low molecular weight, compared to the whole immunoglobulin molecules, and thus, it is advantageous in the preparation, purification and yield of the conjugate. The immunoglobulin Fc region does not contain a Fab fragment, which is highly non-homogenous due to different amino acid sequences according to the antibody subclasses, and thus it can be expected that the immunoglobulin Fc region may greatly increase the homogeneity of substances and be less antigenic.

The term "immunoglobulin Fc region" as used herein, refers to a protein that contains the heavy-chain constant region 2 (CH2) and the heavy-chain constant region 3 (CH3) of an immunoglobulin, excluding the variable regions of the heavy and light chains, the heavy-chain constant region 1 (CH1) and the light-chain constant region 1 (CL1) of the immunoglobulin. It may further include a hinge region at the heavy-chain constant region. Also, the immunoglobulin Fc region of the present invention may be an extended Fc region comprising a part or all of the heavy-chain constant region 1 (CH1) and/or the light-chain constant region 1 (CL1), except for the variable regions of the heavy and light chains, as long as it has a physiological function substantially similar to or better than the native in immunoglobulin. Also, the immunoglobulin Fc region may be a region having a deletion in a relatively long portion of the amino acid sequence of CH2 and/or CH3.

That is, the immunoglobulin Fc region of the present invention may include 1) a CH1 domain, a CH2 domain, a CH3 domain and a 0114 domain, 2) a CH1 domain and a CH2 domain, 3) a CH1 domain and a CH3 domain, 4) a CH2 domain and a CH3 domain, 5) a combination of one or more domains and an immunoglobulin hinge region (or a portion of the hinge region), and 6) a dimer of each domain of the heavy-chain constant regions and the light-chain constant region.

The immunoglobulin Fc region of the present invention includes a native amino acid sequence, and a sequence variant (mutant) thereof. The amino acid sequence variant is a sequence that is different from the native amino acid sequence due to a deletion, an insertion, a non-conservative or conservative substitution or combinations thereof of one or more amino acid residues. For example, in an IgG Fc, amino acid residues known to be important in binding, at positions 214 to 238, 297 to 299, 318 to 322, or 327 to 331, may be used as a suitable target for modification.

Also, other various variants are possible, including one in which a region capable of forming a disulfide bond is deleted, or certain amino acid residues are eliminated at the N-terminal end of a native Fc form or a methionine residue is added thereto. Further, to remove effector functions, a deletion may occur in a complement-binding site, such as a C1q-binding site, and an ADCC (antibody dependent cell mediated cytotoxicity) site. Techniques of preparing such sequence derivatives of the immunoglobulin Fc region are disclosed in international patent publications WO 97/34631 and WO 96/32478.

Amino acid exchanges in proteins and peptides, which do not generally alter the molecular activity, are known in the art (H. Neurath, R. L. Hill, The Proteins, Academic Press, New York, 1979). The most commonly occurring exchanges are Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, Asp/Gly, in both directions.

In addition, the Fc region, if desired, may be modified by phosphorylation, sulfation, acrylation, glycosylation, methylation, farnesylation, acetylation, amidation, etc.

The aforementioned Fc variants are variants that have a biological activity identical to the Fc region of the present invention or improved structural stability, for example, against heat, pH, etc.

In addition, these Fc regions may be obtained from native forms isolated from humans and other animals including cattle, goats, swine, mice, rabbits, hamsters, rats and guinea pigs, or may be recombinants or derivatives thereof, obtained from transformed animal cells or microorganisms. Herein, they may be obtained from a native immunoglobulin by isolating whole immunoglobulins from human or animal organisms and treating them with a proteolytic enzyme. Papain digests the native immunoglobulin into Fab and Fc regions, and pepsin treatment results in the production of pF'c and $F(ab)_2$. These fragments may be subjected to size exclusion chromatography to isolate Fc or pF'c.

The immunoglobulin Fc region may be a recombinant immunoglobulin Fc region, which is a human-derived Fc region obtained from a microorganism.

In addition, the immunoglobulin Fc region may be in the form of having native sugar chains, increased sugar chains compared to a native form, or decreased sugar chains compared to the native form, or may be in a deglycosylated form. The increase, decrease or removal of the immunoglobulin Fc sugar chains may be achieved by methods common in the art, such as a chemical method, an enzymatic method and a genetic engineering method using a microorganism. Here, the removal of sugar chains from an Fc region results in a sharp decrease in binding affinity to the complement (c1q) and a decrease or loss in antibody-dependent cell-mediated cytotoxicity or complement-dependent cytotoxicity, thereby not inducing unnecessary immune responses in vivo. In this regard, an immunoglobulin Fc region in a deglycosylated or aglycosylated form may be more suitable to the object of the present invention as a drug carrier.

As used herein, the deglycosylation refers to an enzymatical removal of sugar moieties from an Fc region, and the aglycosylation refer to an Fc region produced in an unglycosylated form by a prokaryote, specifically *E. coli.*

Meanwhile, the immunoglobulin Fc region may be derived from humans or other animals including cattle, goats, pigs, mice, rabbits, hamsters, rats and guinea pigs, and specifically from humans. In addition, the immunoglobulin Fc region may be an Fe region that is derived from IgG, IgA, IgD, IgE and IgM, or that is made by combinations thereof or hybrids thereof. Specifically, it is derived from IgG or IgM, which are among the most abundant proteins in human blood, and more specifically, derived from IgG, which is known to enhance the half-lives of ligand-binding proteins.

On the other hand, the combination, as used herein, refers to a linkage between a polypeptide encoding a single-chain immunoglobulin Fc region of the same origin and a single-chain polypeptide of a different origin to form a dimer or multimer. That is, a dimer or multimer may be formed from two or more fragments selected from the group consisting of IgG Fc, IgA Fc, IgM Fc, IgD Fc and IgE Fc fragments.

The term "hybrid", as used herein, refers to a presence of sequences encoding two or more immunoglobulin Fc fragments of different origin in a single-chain immunoglobulin Fc region. In the present invention, various types of hybrids are possible. That is, hybrid domains may be composed of one to four domains selected from the group consisting of CH1, CH2, CH3, and CH4 of IgM Fc, Fc, IgA Fc, IgE Fc and IgD Fc, and may include the hinge region.

On the other hand, IgG is divided into IgG1, IgG2, IgG3, and IgG4 subclasses, and the present invention includes combinations and hybrids thereof. IgG2 and IgG4 subclasses may be used, and more specifically, the Fc region of IgG4 rarely having effector functions such as complement dependent cytotoxicity (CDC) may be used. That is, as the drug carrier of the present invention, the a human IgG4-derived non-glycosylated Fc region may be used as an immunoglobulin Fc region. The human-derived Fc region is more preferable than a non-human derived Fc region, which may act as an antigen in the human body and cause undesirable immune responses such as the production of a new antibody against the antigen.

In the present invention, the non-peptidyl polymer refers to a biocompatible polymer including two or more repeating units linked to each other by any covalent bond excluding a peptide bond. Such non-peptidyl polymer may have two ends or three ends.

The non-peptidyl polymer useful in the present invention may be selected from the group consisting of a biodegradable polymer such as polyethylene glycol, polypropylene glycol, ethylene glycol-propylene glycol copolymer, polyoxyethylated polyol, polyvinyl alcohol, polysaccharide, dextran, polyvinyl ethyl ether, polylactic acid (PLA) and polylactic-glycolic acid (PLGA), a lipid polymer, chitin, hyaluronic acid, and a combination thereof, and specifically, polyethylene glycol. In addition, derivatives thereof known in the art and derivatives easily prepared by a method known in the art may be included in the scope of the present invention.

The peptidyl linker used in the fusion protein obtained by a conventional inframe fusion method has drawbacks that it is easily in vivo cleaved by a proteolytic enzyme, and thus a sufficient effect of increasing the half-life of the active drug by a carrier cannot be obtained as expected. In the present invention, however, a non-peptidyl linker as well as the peptidyl linker may be used to prepare the conjugate. In the non-peptidyl linker, a polymer having resistance to the proteolytic enzyme may be used to maintain the half-life of the peptide being similar to that of the carrier. Therefore, any non-peptidyl polymer can be used without limitation, as long as it is a polymer having the aforementioned function, that is, a polymer having resistance to the in vivo proteolytic enzyme. The non-peptidyl polymer has a molecular weight ranging from 1 to 100 kDa, and preferably from 1 to 20 kDa.

The non-peptidyl polymer of the present invention, linked to the immunoglobulin Fc region, may be one polymer or a combination of different types of polymers.

The non-peptidyl polymer used in the present invention has a reactive group capable of binding to the immunoglobulin Fc region and protein drug.

The non-peptidyl polymer has a reactive group at both ends, which is preferably selected from the group consisting of a reactive aldehyde group, a propionaldehyde group, a butyraldehyde group, a maleimide group and a succinimide derivative. The succinimide derivative may be succinimidyl propionate, hydroxy succinimidyl, succinimidyl carboxymethyl, or succinimidyl carbonate. In particular, when the non-peptidyl polymer has a reactive aldehyde group at both ends thereof, it is effective in linking at both ends with a physiologically active polypeptide and an immunoglobulin with minimal non-specific reactions. A final product generated by reductive alkylation by an aldehyde bond is much more stable than that linked by an amide bond. The aldehyde reactive group selectively binds to an N-terminus at a low pH, and binds to a lysine residue to form a covalent bond at high pH, such as pH 9.0.

The reactive groups at both ends of the non-peptidyl polymer may be the same as or different from each other. For example, the non-peptidyl polymer may possess a maleimide group at one end, and an aldehyde group, a propionaldehyde group or a butyraldehyde group at the other end. When a polyethylene glycol having a reactive hydroxy group at both ends thereof is used as the non-peptidyl polymer, the hydroxy group may be activated to various reactive groups by known chemical reactions, or a commercially available polyethylene glycol having a modified reactive group may be used so as to prepare the conjugate of the present invention.

The kind and preparation method of the long-acting secretory peptide conjugate are described in detail in Korean Patent Nos. 10-1058290, 10-1231431, and 10-1058315.

In an embodiment of the present invention, lysine (Lys) of imidazo-acetyl exendin-4(CA exendin-4) was modified with PEG, and PEG-modified exendin-4 was linked to the immunoglobulin Fc, thereby preparing a long-acting exendin-4 conjugate (Example 9).

Such long-acting insulin analogue conjugate and the long-acting insulinotropic peptide of the present invention remarkably increase in vivo duration of efficacy and show similar in vivo half-life. Thus, combination administration thereof is useful in the treatment of diabetes.

Combination administration of the long-acting insulin analogue conjugate and the long-acting insulinotropic peptide conjugate of the present invention can exhibit excellent effects of controlling the blood glucose level and improving the blood lipid compared to a single administration. In one embodiment of the present invention, it was confirmed that combination administration of the long-acting insulin analogue conjugate and the long-acting insulinotropic peptide (i.e., exendin-4) conjugate can improve lipotoxicity and glucotoxicity, thus maintaining the beta cell mass and further inhibiting the progression of diabetes. Such results suggest that a composite composition of the long-acting insulin analogue conjugate and the long-acting insulinotropic peptide conjugate according to the present invention, or combination administration of the conjugates can significantly reduce the lipotoxicity associated with an increase in the blood lipid levels, and the glucotoxicity associated with an increase in hood glucose levels due to insufficient control of blood glucose levels, which are side-effects that incur in some diabetic patients upon a single administration of insulin or insulinotropic peptide, and further the progression of diabetes can be significantly alleviated through the prevention of abnormality in the function of pancreatic beta cells and/or increase in the pancreatic beta cell mass, thus leading to improvement, treatment, and prevention of diabetes and improvement of the the prognosis of diabetes.

The composition of the present invention is characterized by combination administration of the long-acting insulin analogue conjugate and the long-acting insulinotropic peptide conjugate.

When the combination administration of the long-acting insulin analogue conjugate and the long-acting insulinotropic peptide conjugate of the present invention is performed, the long-acting insulin analogue conjugate acts on the insulin receptor and the long-acting insulinotropic peptide conjugate acts on the glucagon like peptide-1 receptor simultanesouly, so that the blood glucose level is lowered and a stable blood glucose level is maintained, compared to single administration thereof. The combination administration of the conjugates has the effects of reducing the risk of hypoglycemia and weight gain which can be induced by single administration of insulin, and also reduces the dose of the total insulin owing to the action of the insulinotropic peptide. There is an advantage that the dose of the insulinotropic peptide such as exendin-4 can also be reduced to prevent adverse effects such as nausea and vomiting caused by single administration of exendin-4. The use of the long-acting insulin analogue conjugate and the long-acting insulinotropic peptide conjugate remarkably increases the blood half-life and in vivo duration of efficacy, so that the treatment frequency is reduced to improve quality of life in chronic patients that suffer from daily injections. Thus, it is very useful for the treatment of diabetes. Further, the pharmaceutical composition of the present invention shows excellent duration of in vivo efficacy and titers, and the dose can be greatly reduced upon combination administration.

Furthermore, unlike the conventional formulations, the composition of the present invention is characterized in that it can alleviate a function loss of the pancreatic beta cells and a decrease in the pancreatic beta cell mass due to an apoptosis of the pancreatic beta-cells incurred in diabetic patients. This can reduce the decrease in the function and mass of beta cells through the reduction and complementary action of the lipotoxicity and glucotoxicity, thus inhibiting the progression of diabetes. By doing so, the composition of the present invention can alleviate the side effects of pancreatic cells in diabetic patients.

The long-acting insulin analogue conjugate and the long-acting insulinotropic peptide conjugate may be administered simultaneously, sequentially or reversely, and may be administered simultaneously in a proper combination of effective doses. Specifically, the long-acting insulin analogue conjugate and the long-acting insulinotropic peptide conjugate may be stored separately in individual containers, and then administered simultaneously, sequentially or reversely.

Further, the long-acting insulin analogue conjugate and the long-acting insulinotropic peptide conjugate as the composition for combination administration of the present invention may be in a form of a therapeutic kit for diabetes that includes the conjugates in a single container or separately in individual containers. The kit may include a pharmaceutically acceptable carrier and an instruction manual for using the kit.

Further, the long-acting insulin analogue conjugate and the long-acting insulintropic peptide conjugate may be administered in combination with the insulinotropic peptide and insulin, respectively. The long-acting insulin analogue conjugate may be administered in combination with the insulinotropic peptide such as GLP-1 agonists (e.g., Exenatide, Liraglutide, Lixisenatide), and the long-acting insulinotropic peptide conjugate may be administered in combination with insulin and insulin analogue, basal insulin.

As used herein, the term “diabetes” or “diabetes mellitus” refer to a metabolic disease caused by a lack of insulin secretion or abnormality in insulin function. Combination administration of the composition of the present invention to a subject is performed to control the blood glucose levels, thereby treating diabetes. Also, the composition of the present invention can be used as a therapeutic agent for diabetes, which can maintain and increase the function and the cell mass of the pancreatic beta cells, and provide safety from side effects such as potential beta cell stress. In addition, the composition of the present invention can significantly reduce lipotoxicity and glucotoxicity, which causes of the decrease in the function and mass of beta cells, and can alleviate the progression of diabetes. Therefore, the composition of the present invention cam remarkably improve side effects of the conventional drugs.

As used herein, the term “prevention” refers to all of the actions by which the occurrence of diabetes or pancreatic beta cell side effects is restrained or retarded by combination administration of the composition of the present invention, and the term “treatment” refers to all of the actions by which the symptoms of diabetes or pancreatic beta cell side effects have taken a turn for the better or been modified favorably by combination administration of the composition of the present invention. The treatment of diabetes and the prevention or treatment of pancreatic beta cell side effects may be applied to any mammal that may have diabetes, and examples thereof include humans and primates as well as livestock such as cattle, pig, sheep, horse, dog, and cat without limitation, and specifically human.

As used herein, the term “administration” refers to introduction of a predetermined amount of a substance into a patient by a certain suitable method. The composition may be administered via any of the common routes, as long as it is able to reach a desired tissue. A variety of modes of administration are contemplated, including intraperitoneal, intravenous, intramuscular, subcutaneous, intradermal, oral, topical, intranasal, intrapulmonary and intrarectal, but the present invention is not limited to these exemplary modes of administration. However, since peptides are digested upon oral administration, active ingredients of a composition for oral administration should be coated or formulated for protection against degradation in the stomach. Specifically, the composition may be administered in an injectable form. In addition, the long-acting agent may be administered using a certain apparatus capable of transporting the active ingredients into a target cell.

Further, the pharmaceutical composition of the present invention may be determined by several related factors including the types of diseases to be treated, administration routes, the patient’s age, gender, weight and severity of the illness, as well as by the types of the drug used as an active component.

Further, the pharmaceutical composition of the present invention may include a pharmaceutically acceptable carrier. As used herein, the term “pharmaceutically acceptable carrier” refers to a carrier or diluent that does not cause significant irritation to an organism and does not abrogate the biological activity and properties of the administered compound. For oral administration, the pharmaceutically acceptable carrier may include a binder, a lubricant, a disintegrant, an excipient, a solubilizer, a dispersing agent, a stabilizer, a suspending agent, a coloring agent, or a flavor. For injectable preparations, the pharmaceutically acceptable carrier may include a buffering agent, a preserving agent, an analgesic, a solubilizer, an isotonic agent, and a stabilizer. For preparations for topical administration, the pharmaceutically acceptable carrier may include a base, an excipient, a lubricant, and a preserving agent. The pharmaceutical composition of the present invention may be formulated into a variety of dosage forms in combination with the aforementioned pharmaceutically acceptable carriers. For example, for oral administration, the pharmaceutical composition may be formulated into tablets, troches, capsules, elixirs, suspensions, syrups or wafers. For injectable preparations, the pharmaceutical composition may be formulated into an ampule as a single-dose dosage form or a multi-dose container. The pharmaceutical composition may be also formulated into solutions, suspensions, tablets, pills, capsules and long-acting preparations.

On the other hand, examples of the carrier, the excipient, and the diluent suitable for formulations include lactose, dextrose, sucrose, sorbitol, mannitol, xylitol, erythritol, maltitol, starch, acacia, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oils. In addition, the pharmaceutical formulations may further include fillers, anti-coagulating agents, lubricants, humectants, flavors, and antiseptics.

In another aspect, the present invention provides a method for preventing or treating diabetes, including the step of administering the composition including the long-acting insulin analogue conjugate and the long-acting insulinotropic peptide conjugate to a subject having diabetes or at risk of having diabetes.

In one embodiment, the present invention provides a method for reducing one or more of the pancreatic beta cell side-effects selected from the group consisting of lipotoxicity, glucotoxicity, abnormality in the function of pancreatic beta cells and reduction in the pancreatic beta cell mass in diabetic patients, including a step of administering the composition containing the long-acting insulin analogue conjugate and the long-acting insulinotropic peptide conjugate to the patients suffering from diabetes.

The administration step may be performed by combination administration of the long-acting insulin analogue conjugate and the long-acting insulinotropic peptide conjugate, but is not limited to, simultaneously, sequentially or reversely, and the conjugates may be administered simultaneously in a proper combination of effective doses.

Although administered only once a week, the composition including both of the long-acting insulin analogue conjugate and the long-acting insulinotropic peptide conjugate of the present invention can exhibit excellent improvement in the blood glucose levels and causes no side effect of weight gain, and thus the composition may be used for the prevention or treatment of diabetes.

In one embodiment, the present invention provides a method for improving and/or reducing lipotoxicity and/or glucotoxicity in diabetic patients, including a step of administering the said composition containing the long-acting insulin analogue conjugate and the long-acting insulinotropic peptide conjugate to the patient suffering from diabetes.

In one embodiment, the present invention provides a method for improving a function of pancreatic beta cells and/or preserving and/or increasing a pancreatic beta cell mass, including a step of administering the said composition containing the long-acting insulin analogue conjugate and the long-acting insulinotropic peptide conjugate to patients suffering from diabetes.

Hereinafter, the present invention will be described in more detail with reference to Examples. However, these Examples are for illustrative purposes only, and the invention is not intended to be limited by these Examples.

Example 1: Preparation of Single Chain Insulin Analogue Expression Vector

In order to prepare insulin analogues (analog), each analogue having a variant of one amino acid in A chain or B chain, using the available native insulin expression vector as a template, forward and reverse oligonucleotides were synthesized (Table 2), and PCR was performed to amplify respective analogue genes.

Each of the amino acid sequences modified in A chain or B chain and each name of the analogues are given in the following Table 1. That is, analogue 1 has a substitution of alanine for glycine at position 1 of A chain, and analogue 4 has a substitution of alanine for glycine at position 8 of B chain.

TABLE 1

| Analog | Modifed sequence |
|---|---|
| Analog 1 | $A^1G \rightarrow A$ |
| Analog 2 | $A^2I \rightarrow A$ |
| Analog 3 | $A^{19}Y \rightarrow A$ |
| Analog 4 | $B^8G \rightarrow A$ |
| Analog 5 | $B^{23}G \rightarrow A$ |
| Analog 6 | $B^{24}F \rightarrow A$ |
| Analog 7 | $B^{25}F \rightarrow A$ |
| Analog 8 | $A^{14}Y \rightarrow E$ |
| Analog 9 | $A^{14}Y \rightarrow N$ |

Primers for insulin analogue amplification are given in the following Table 2.

TABLE 21

| Analog | Sequence | SEQ ID NO |
|---|---|---|
| Analog 1 | 5' GGGTCCCTGCAGAAGCGTGCGATTGTGGAACAATGCTGT 3' | SEQ ID NO 1 |
| | 5' ACAGCATTGTTCCACAATCGCACGCTTCTGCAGGGACCC 3' | SEQ ID NO 2 |
| Analog 2 | 5' TCCCTGCAGAAGCGTGGCGCGGTGGAACAATGCTGTACC 3' | SEQ ID NO 3 |
| | 5' GGTACAGCATTGTTCCACCGCGCCACGCTTCTGCAGGGA 3' | SEQ ID NO 4 |
| Analog 3 | 5' CTCTACCAGCTGGAAAACGCGTGTAACTGAGGATCC 3' | SEQ ID NO 5 |
| | 5' GGATCCTCAGTTACACGCGTTTTCCAGCTGGTAGAG 3' | SEQ ID NO 6 |
| Analog 4 | 5' GTTAACCAACACTTGTGTGCGTCACACCTGGTGGAAGCT 3' | SEQ ID NO 7 |
| | 5' AGCTTCCACCAGGTGTGACGCACACAAGTGTTGGTTAAC 3' | SEQ ID NO 8 |
| Analog 5 | 5' CTAGTGTGCGGGGAACGAGCGTTCTTCTACACACCCAAG 3' | SEQ ID NO 9 |
| | 5' CTTGGGTGTGTAGAAGAACGCTCGTTCCCCGCACACTAG 3' | SEQ ID NO 10 |
| Analog 6 | 5' GTGTGCGGGGAACGAGGCGCGTTCTACACACCCAAGACC 3' | SEQ ID NO 11 |
| | 5' GGTCTTGGGTGTGTAGAACGCGCCTCGTTCCCCGCACAC 3' | SEQ ID NO 12 |
| Analog 7 | 5' TGCGGGGAACGAGGCTTCGCGTACACACCCAAGACCCGC 3' | SEQ ID NO 13 |
| | 5' GCGGGTCTTGGGTGTGTACGCGAAGCCTCGTTCCCCGCA 3' | SEQ ID NO 14 |
| Analog 8 | 5' CCAGCATCTGCTCCCTCGAACAGCTGGAGAACTACTG 3' | SEQ ID NO 15 |
| | 5' Cagtagttctccagctgttcgagggagcagatgctgg 3' | SEQ ID NO 16 |
| Analog 9 | 5' CAGCATCTGCTCCCTCAACCAGCTGGAGAACTAC 3' | SEQ ID NO 17 |
| | 5' Gtagttctccagctggttgagggagcagatgctg 3' | SEQ ID NO 18 |

PCR for insulin analogue amplification was performed under conditions of at 95° C. for 30 seconds, at 55° C. for 30 seconds, and at 68° C. for 6 minutes for 18 cycles. In order to express the insulin analogue fragments obtained under the conditions as intracellular inclusion bodies, each of them was inserted into pET22b vector, and the expression vectors thus obtained were designated as pET22b-insulin analogues 1 to 9, respectively. The respective expression vectors included nucleic acids encoding amino acid sequences of insulin analogues 1 to 9 under control of T7 promoter, and expressed insulin analogues as inclusion bodies in host cells, respectively.

DNA sequences and protein sequences of insulin analogues 1 to 9 are given in the following Table 3.

TABLE 3

| Analog | | Sequence | SEQ ID NO |
|---|---|---|---|
| Analog 1 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GCG ATT GTG GAA CAA TGC TGT ACC AGC ATC TGC TCC CTC TAC CAG CTG GAG AAC TAC TGC AAC | 19 |
| | protein | Phe Val Asn Gln His Leu Cys Gly Ser His Leu Val Glu Ala Leu Tye Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg **Ala** Ile Val Glu Gln Cys Cys Thr Ser Ile Cys Ser Leu Tyr Gln Leu Glu Asn Tyr Cys Asn | 20 |
| Analog 2 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 21 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly **Ala** Val Glu Gln Cys Cys Thr Ser Ile Cys Ser Leu Tyr Gln Leu Glu Asn Tyr Cys Asn | 22 |
| Analog 3 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 23 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu **Asn** Ala Cys Asn | 24 |
| Analog 4 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 25 |
| | Protein | Phe Val Asn Gln His Leu Cys Ala Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 26 |

TABLE 3-continued

| Analog | | Sequence | SEQ ID NO |
|---|---|---|---|
| Analog 5 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 27 |
| | Protein | Phe Val Asn Gln His Leu Cys Gly Ser His Leu Val Glu Ala Leu Tyr Leu Val Cys Gly Glu Arg **Ala** Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 28 |
| Analog 6 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 29 |
| | Protein | Phe Val Asn Gln His Leu Cys Gly Ser His Leu Val Glu Ala Leu Tyr Leu Val Cys Gly Glu Arg Gly **Ala** Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 30 |
| Analog 7 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 31 |
| | Protein | Phe Val Asn Gln His Leu Cys Gly Ser His Leu Val Glu Ala Leu Tyr Leu Val Cys Gly Glu Arg Gly Phe **Ala** Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu Tyr Gln Leu Glu Asn Tyr Cys Asn | 32 |
| Analog 8 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 33 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu **Glu** Gln Leu Glu Asn Tyr Cys Asn | 34 |
| Analog 9 | DNA | TTC GTT AAC CAA CAC TTG TGT GGC TCA CAC CTG GTG GAA GCT CTC TAC CTA GTG TGC GGG GAA CGA GGC TTC TTC TAC ACA CCC AAG ACC CGC CGG GAG GCA GAG GAC CTG CAG GTG GGG CAG GTG GAG CTG GGC GGG GGC CCT GGT GCA GGC AGC CTG CAG CCC TTG GCC CTG GAG GGG TCC CTG CAG AAG CGT GGC GCG GTG GAA CAA TGC TGT ACC AGC ATC TGC TCC CTC TAC CAG CTG GAG AAC TAC TGC AAC | 35 |
| | Protein | Phe Val Asn Gln His Leu Cys Gly Ser His Leu Val Glu Ala Leu Tyr Leu Val Cys Gly Glu Arg Gly Phe Phe Tyr Thr Pro Lys Thr Arg Arg Glu Ala Glu Asp Leu Gln Val Gly Gln Val | 36 |

TABLE 3-continued

| Analog | Sequence | SEQ ID NO |
|---|---|---|
| | Glu Leu Gly Gly Gly Pro Gly Ala Gly Ser Leu Gln Pro Leu Ala Leu Glu Gly Ser Leu Gln Lys Arg Gly Ile Val Glu Gln Cys Cys Thr Ser Ile Cys Ser Leu **Asn** Gln Leu Glu Asn Tyr Cys Asn | |

Example 2: Expression of Recombinant Insulin Analogue Fusion Peptides

Recombinant insulin analogues were expressed under control of T7 promoter. *E. coli* BL21-DE3 (*E. coli* B F-dcm ompT hsdS(rB-mB-) gal DE3); Novagen) was transformed with each of the recombinant insulin analogue expression vectors. Transformation was performed in accordance with the procedures recommended by Novagen. Single colonies transformed with the respective recombinant expression vectors were inoculated in ampicillin (50/ml)-containing 2× Luria Broth (LB) medium, and cultured at 37° C. for 1.5 hours. Each culture broth of the recombinant strain and 30% glycerol-containing 2× LB medium were mixed at a ratio of 1:1(v/v), and each 1 ml thereof was dispensed to a cryotube, and stored at −140° C. These samples were used as cell stocks for production of the recombinant fusion proteins.

To express recombinant insulin analogues, each 1 vial of the cell stocks was thawed and inoculated in 500 ml of 2× Luria Broth, and cultured under shaking at 37° C. for 14~16 hours. When OD600 value reached 5.0 or higher, the culture was terminated and the culture broth was used as a seed culture. The seed culture was inoculated to a 50 L fermentor (MSJ-U2, B. E. MARUBISHI, Japan) containing 17 L of fermentation medium to begin initial bath fermentation. The culture conditions were maintained at 37° C., an air flow rate of 20 L/min (1 vvm), and an agitation speed of 500 rpm with a pH adjusted to 6.70 with ammonia. Fermentation was performed in a fed-hatch mode by further adding a feeding solution when nutrients in the culture broth were depleted. The cell growth was monitored by OD measurement. At an OD value above 100 or higher, IPTG was introduced at a final concentration of 500 M. After introduction, culture was further performed for about 23~25 hours. After terminating the culture, recombinant strains were collected using a centrifuge, and stored at −80° C. until use.

Example 3: Recover and Refolding of Recombinant Insulin Analogues

In order to convert the recombinant insulin analogues expressed in Example 2 into soluble forms, cells were disrupted, followed by refolding. 100 g (wet weight) of the cell pellet was re-suspended in 1 L of lysis buffer (50 mM Tris-HCl (pH 9.0), 1 mM EDTA (pH 8.0), 0.2 M NaCl and 0.5% Triton X-100). The cells were disrupted using a microfluidizer processor M-110EH (AC Technology Corp. Model M1475C) at an operating pressure of 15,000 psi. The cell lysate thus disrupted was centrifuged at 7,000 rpm and 4° C. for 20 minutes. The supernatant was discarded and the pellet was re-suspended in 3 L of washing buffer (0.5% Triton X-100 and 50 nmol Tris-HCl (pH 8.0), 0.2 M NaCl, 1 mM EDTA). After centrifugation at 7,000 rpm and 4° C. for 20 minutes, the cell pellet was re-suspended in distilled water, followed by centrifugation in the same manner. The pellet thus obtained was re-suspended in 400 ml of buffer (1 M Glycine, 3.78 g Cysteine-HCl, pH 10.6) and stirred at room temperature for 1 hour. To recover the recombinant insulin analogue thus re-suspended, 400 mL of 8 M urea was added and stirred at 40° C. for 1 hour. For refolding of the solubilized recombinant insulin analogues, centrifugation was carried out at 7,000 rpm and 4° C. for 30 minutes, and the supernatant was collected. 2 L of distilled water was added thereto using a peristaltic pump at a flow rate of 1000 ml/hr while stirring at 4° C. for 16 hours.

Example 4: Cation Binding Chromatography Purification

The refolded sample was loaded onto a Source S (GE healthcare) column equilibrated with 20 mM sodium citrate (pH 2.0) buffer containing 45% ethanol, and then the insulin analogue proteins were eluted in 10 column volumes with a linear gradient from 0% to 100% 20 mM sodium citrate (pH 2.0) buffer containing 0.5 M potassium chloride and 45% ethanol.

Example 5: Trypsin and Carboxypeptidase B Treatment

Salts were removed from the eluted samples using a desalting column, and the buffer was exchanged with a buffer (10 mM Tris-HCl, pH 8.0). With respect to the obtained sample protein, trypsin corresponding to 1000 molar ratio and carboxypeptidase B corresponding to 2000 molar ratio were added, and then stirred at 16° C. for 16 hours. To terminate the reaction, 1 M sodium citrate (pH 2.0) was used to lower the pH to 3.5.

Example 6: Cation Binding Chromatography Purification

The sample thus reacted was loaded onto a Source S (GE healthcare) column equilibrated with 20 mM sodium citrate (pH 2.0) buffer containing 45% ethanol, and then the insulin analogue proteins were eluted in 10 column volumes with a linear gradient from 0% to 100% 20 mM sodium citrate (pH 2.0) buffer containing 0.5 M potassium chloride and 45% ethanol.

Example 7: Anion Binding Chromatography Purification

Salts were removed from the eluted sample using a desalting column, and the buffer was exchanged with a buffer (10 mM Tris-HCl, pH 7.5). In order to isolate pure insulin analogues from the sample obtained in Example 6, the sample was loaded onto an anion exchange column (Source Q: GE healthcare) equilibrated with 10 mM Tris (pH 7.5) buffer, and the insulin analogue protein was eluted in 10 column volumes with a linear gradient from 0% to 100% 10 mM Tris (pH 7.5) buffer containing 0.5 M sodium chloride.

Purity of the insulin analogue thus purified was analyzed by protein electrophoresis (SDS-PAGE) and high pressure chromatography (HPLC), and modifications of amino acids were identified by peptide mapping and molecular weight analysis of each peak.

As a result, each insulin analogue was found to have the desired change in its amino acid sequence.

Example 8: Preparation of Long-Acting Insulin Analogue

In this Example, a long-acting conjugate of a sequence analogue (Glu at position 14 of A chain) of native insulin as a representative insulin analogue was prepared.

To pegylate the N-terminus of the beta chain of the insulin analogue using 3.4K ALD2 PEG (NOF, Japan), the insulin analogue and PEG were reacted at a molar ratio of 1:4 with an insulin analogue concentration of 5 at 4-8° C. for about 2 hours. In this regard, the reaction was performed in 50 mM sodium citrate at pH 6.0 and 40-60% isopropanol. 3.0~20.0 mM sodium cyanoborohydride was added as a reducing agent and was allowed to react. The reaction solution was purified with SP-HP (GE Healthcare, USA) column using a buffer containing sodium citrate (pH 3.0) and ethanol, and KCl concentration gradient.

To prepare an insulin analogue-immunoglobulin Fc fragment conjugate, the purified mono-PEGylated insulin analogue and the immunoglobulin Fc fragment were reacted at a molar ratio of 1:1 to 1:2 and at 25° C. for 12~16 hrs, with a total protein concentration of about 20 mg/ml. In this regard, the reaction buffer conditions were 100 mM HEPES at pH 8.2, and 20 mM sodium cyanoborohydride as a reducing agent was added thereto. Therefore, an insulin analogue conjugate PEGylated at the N-terminus of the Fc fragment was prepared.

Upon termination of the reaction, the reaction solution was loaded onto the Q HP (GE Healthcare, USA) column with Tris-HCl (pH 7.5) buffer and NaCl concentration gradient to perform primary purification of the insulin analogue-immunoglobulin Fc fragment conjugate.

Thereafter, Source 15ISO (GE Healthcare, USA) was used as a secondary column to obtain the insulin analogue-immunoglobulin Fc fragment conjugate. In this regard, the insulin analogue-immunoglobulin Fc fragment conjugate was eluted using a concentration gradient of ammonium sulfate containing Tris-HCl (pH 7.5).

Example 9: Preparation of Lone-Acting Exendin-4 Conjugate 3.4k PropionALD (2) PEG was reacted with the lysine (Lys) of CA exendin-4 using imidazo-acetyl exendin-4 (CA exendin-4, AP, USA). Among the two Lys isomer peaks, the last isomer peak (positional isomer of Lys27), which has more reaction and which is easily distinguishable from the N-terminal isomer peaks, was used for the coupling reaction.

The reaction was performed at a molar ratio of peptide: immunoglobulin Fc of 1:8, and a total concentration of proteins of 60/at 4° C. for 20 hrs. The reaction was performed in a solution of 100 mM K-P (pH 6.0), and 20 mM SCB was added as a reducing agent. The coupling reaction solution was purified through two purification columns. First, SOURCE Q (XK 16 mL, Amersham Biosciences) was used to remove a large amount of immunoglobulin Fc which had not participated in the coupling reaction. Using 20 mM Tris (pH 7.5) and 1 M NaCl with salt gradients, the immunoglobulin Fc having relatively weak binding force was eluted first, and then the exendin-4-immunoglobulin Fc was eluted immediately thereafter. Through this first purification process, the immunoglobulin Fc was removed to some extent, but since the immunoglobulin Fc and the exendin-4-immunoglobulin Fc have similar binding power to each other in the ion exchange column, they could not be completely separated from each other. Accordingly, secondary purification was performed based on the difference in hydrophobicity between the two materials. Using 20 mM Tris (pH7.5) and 1.5 M ammonium sulfate in SOURCE ISO (HR 16 mL. Amersham Biosciences), the first purified samples were coupled, and the sample mixture was eluted while gradually reducing the concentration of ammonium sulfate. In the HIC Column, the immunoglobulin Fc having weak binding power was eluted first, and then the exendin-4-immunoglobulin Fc sample having strong binding power was eluted later. Since they have prominently different hydrophobicity, they can be more easily separated from each other than in the ion exchange column.

Column: SOURCE Q (XK 16, Amersham Biosciences)

Flow rate: 2.0/min

Gradient: A0→25% 70 min B (A: 20 mM Tris pH 7.5, B: A+1M NaCl)

Column: SOURCE ISO (HR 16, Amersham Biosciences)

Flow rate: 7.0/min

Gradient: B 100→0% 60 min B (A: 20 mM Tris pH 7.5, B: A+1.5M ammonium sulfate)

Example 10: Efficacy of Controlling Blood Glucose and Changes in Body Weight (ΔBody Weight) in Type 2 Diabetic Mouse By Combination Administration of Long-Acting Insulin Analogue Conjugate and Long-Acting Exendin-4 Conjugate In order to test in vivo efficacy by administration of the compositions including the long-acting insulin analogue conjugate and the long-acting exendin-4 conjugate prepared in Examples 8 and 9 or combination administration of the long-acting insulin analogue conjugate and the long-acting exendin-4 conjugate, type 2 diabetic db/db mouse was used. Since db/db mouse (BKS.Cg−+$Lepr^{db}$/+$Lepr^{db}$/OlaHsd mouse) shows diabetic symptoms similar as in human by removal of leptin receptor, it was used in this Example.

1-2 drops of blood were taken from the caudal vein of 8-week-old db/db mouse using a 26 G syringe, and the blood glucose level was measured using a glucometer (OneTouch Ultra, LifeScan, Inc., USA). Diabetes induction was determined by the measured blood glucose (350-600/). Diabetes-induced mice were divided into five groups of G1, G2, G3, G4, and G5, each group having five or six mice.

The groups were divided into a non-treated control group (Vehicle), a long-acting insulin analogue conjugate-treated group (8.8 nmol/kg), a long-acting exendin-4 conjugate-treated group (0.36 nmol/kg), a long-acting insulin analogue conjugate (2.2 nmol/kg) and long-acting exendin-4 conjugate (0.36 nmol/kg)-treated group, and a long-acting insulin analogue conjugate (8.8 nmol/kg) and long-acting exendin-4 conjugate (0.36 nmol/kg) treated group. After repeated administration of the above test materials for 5 weeks, glycosylated hemoglobin (HbA1c) levels were measured in each group. Glycosylated hemoglobin is normally formed in erythrocytes by the reaction of glucose with hemoglobin. When blood glucose levels maintain high, glycosylated hemoglobin levels also increase. The mouse glycosylated hemoglobin level reflects an average blood glucose level for 4-5 weeks, and thus it is useful in the measurement of capability for controlling blood glucose level of the test material. Further, changes in body weight (ΔBW) of the test animal prior to the drug treatment and on the last day of the experiment were calculated.

As a result, the combination administration of the long-acting insulin analogue conjugate and the long-acting exendin-4 conjugate showed a reduction in glycosylated hemoglobin level (FIG. 1), which is a remarkable improvement, compared to single administration of the long-acting insulin analogue conjugate or the long-acting exendin-4 conjugate. Further, although the administration dose of the insulin analogue conjugate was lowered to ¼, the effect of the combination administration was maintained.

Figure 2:
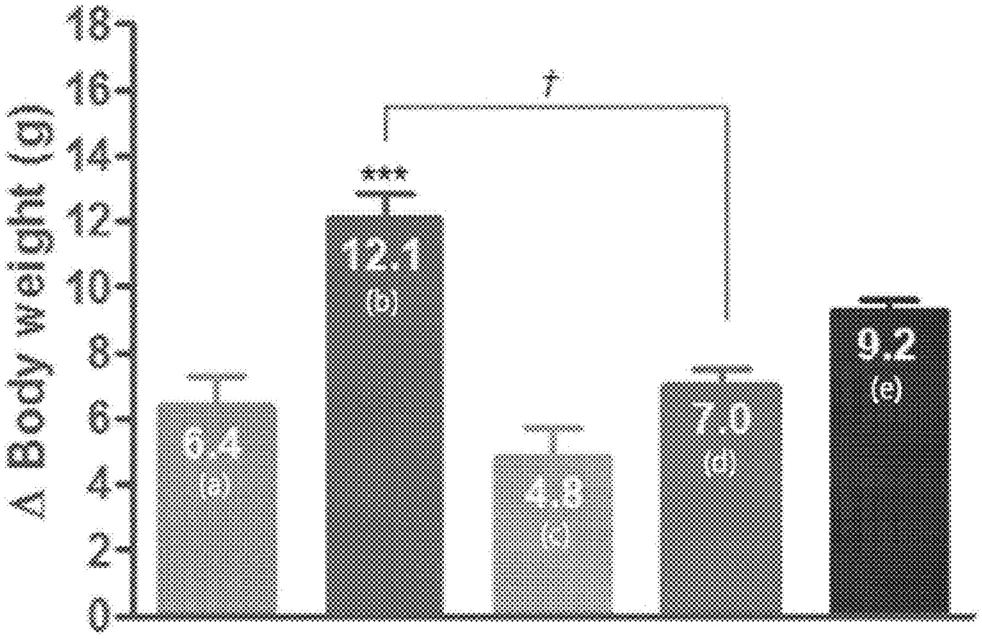
FIG. 2 is a graph showing changes in body weight (BW) after combination administration of the long-acting insulin analogue conjugate and the long-acting exendin-4 conjugate to db/db mice (*P<0.05, P<0.01, *P<0.001 by Dunnet's MC test) (†P<0.05, †† P<0.01, †††P<0.001 by Dunnet's MC test, vs. single administration of long-acting insulin analogue.

The measurement results of ΔBody weight showed that combination administration of the long-acting insulin analogue conjugate and the long-acting exendin-4 conjugate showed an effect of alleviating weight gain, compared to single administration of the long-acting insulin analogue conjugate (FIG. 2). Further, when the administration dose of the long-acting insulin analogue conjugate was lowered to ¼, the effect of alleviating weight gain was remarkably increased.

These results show that combination administration of the long-acting insulin analogue conjugate and the long-acting exendin-4 conjugate of the present invention exhibits excellent effect of controlling blood glucose level, compared to single administration thereof. Further, the effect of controlling blood glucose level by combination administration thereof was maintained, even though the administration dose of the insulin analogue conjugate was lowered. Further, as the administration dose of the long-acting insulin analogue conjugate was lowered to ¼, the weight gain was remarkably reduced, indicating that combination administration of the long-acting insulin analogue conjugate and the long-acting exendin-4 conjugate remarkably reduces the risk of hypoglycemia as well as weight gain, owing to the reduction in the dose of insulin.

Example 11: Efficacy of Maintaining the Beta Cell Mass in Type 2 Diabetic Mouse By Combination Administration of Long-Acting Insulin Analogue Conjugate and Long-Acting Exendin-4 Conjugate In order to test in vivo efficacy by administration of the composition including the long-acting insulin analogue conjugate (long-acting insulin derivative conjugate) and the long-acting exendin-4 (an example of the long-acting insulinotropic) conjugate or by combination administration of the long-acting insulin analogue conjugate and the long-acting exendin-4 conjugatea type 2 diabetic db/db mouse was used.

As the insulin analogue of the long-acting insulin derivative conjugate used in this example, the analogue 8($A^{14}$Y→E) in Table 1 was used and as the long-acting insulinotropic peptide, the long-acting exendin-4 conjugate including the imidazo-acetyl exendin-4 (CA Exendin-4) was used. The lysine of extendin-4 was modified with PEG, and the PEG-modified exendin-4 was linked to an immunoglobulin Fc to produce a long-acting exendin-4 conjugate. In particular, CA exendin-4 and insulin analogue 8 were reacted in a molar ratio of 1.01 to 1:50 to produce a conjugate thereof.

Since db/db mouse (BKS.Cg−+$Lepr^{db}$/+$Lepr^{db}$/OlaHsd mouse) shows diabetic symptoms similar to those in humans by removal of leptin receptor, the mouse was used in this Example.

1-2 drops of blood were taken from the tail vein of 12-week-old db/db mouse using a 26 G syringe, and the blood glucose level was measured using a glucometer (OneTouch Ultra, LifeScan, Inc., USA). Diabetes induction was determined by the measured blood glucose(Non-diabetic normal range was about 100-150 mg/dl, and mice with a blood glucose level of greater than 350 mg/dl were selected and used for the accuracy of the Example). Diabetes-induced mice were divided into seven groups of G1, G2, G3, G4, G5, G6 and G7, each group having seven or eight mice.

The groups were divided into a non-treated control group (Vehicle), long-acting insulin analogue conjugates-treated two groups by dose (4.2 nmol/kg, 8.4 nmol/kg), a long-acting exendin-4 conjugate-treated group (0.36 nmol/kg), a combination administration group of a long-acting insulin analogue conjugate (4.2 nmol/kg) and long-acting acting exendin-4 conjugate (0.36 nmol/kg), and a combination administration group of long-acting insulin analogue conjugate (8.4 nmol/kg) and long-acting exendin-4 conjugate (0.36 nmol/kg)-treated group.

After repeated administration of the above test materials at a dose described above at two day intervals for 12 weeks, glycosylated hemoglobin (HbA1c) levels were measured in each group. Glycosylated hemoglobin is a form of hemoglobin, which are normally present in erythrocytes, to which a glucose is hound. When blood glucose levels are maintained high, glycosylated hemoglobin levels also increase. The mouse glycosylated hemoglobin level reflects an average blood glucose level for 4-5 weeks, and thus it is useful in the measurement of the capability for controlling blood glucose level of the test materials. After 12 weeks repeated drug administration, the blood was collected from the mice orbital vein and the serum triglyceride concentration was measured from the collected serum. After autopsy of each subject, the pancreas was taken to measure the beta cell mass.

Figure 5:
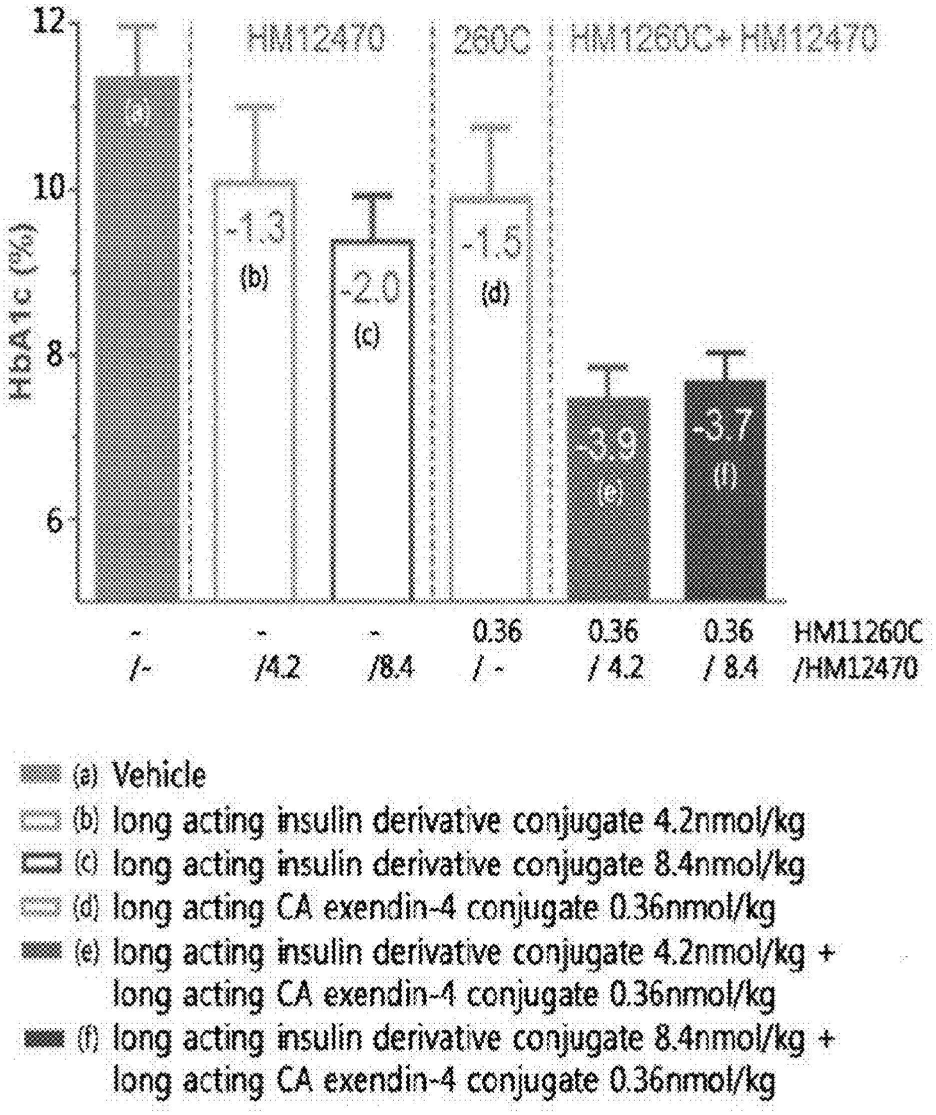
FIG. 5 is a graph showing glycosylated hemoglobin (HbA1c) levels, which are measured to examine blood glucose control by combination administration of a long-acting insulin analogue conjugate and a long-acting exendin-4 conjugate to a db/db mouse.

As a result, combination administration of the long-acting insulin analogue conjugate and the long-acting exendin-4 conjugate showed a reduction in glycosylated hemoglobin level (FIG. 5), which is a remarkable improvement, compared to single administration of a long-acting insulin analogue conjugate or a long-acting exendin-4 conjugate.

Figure 4:
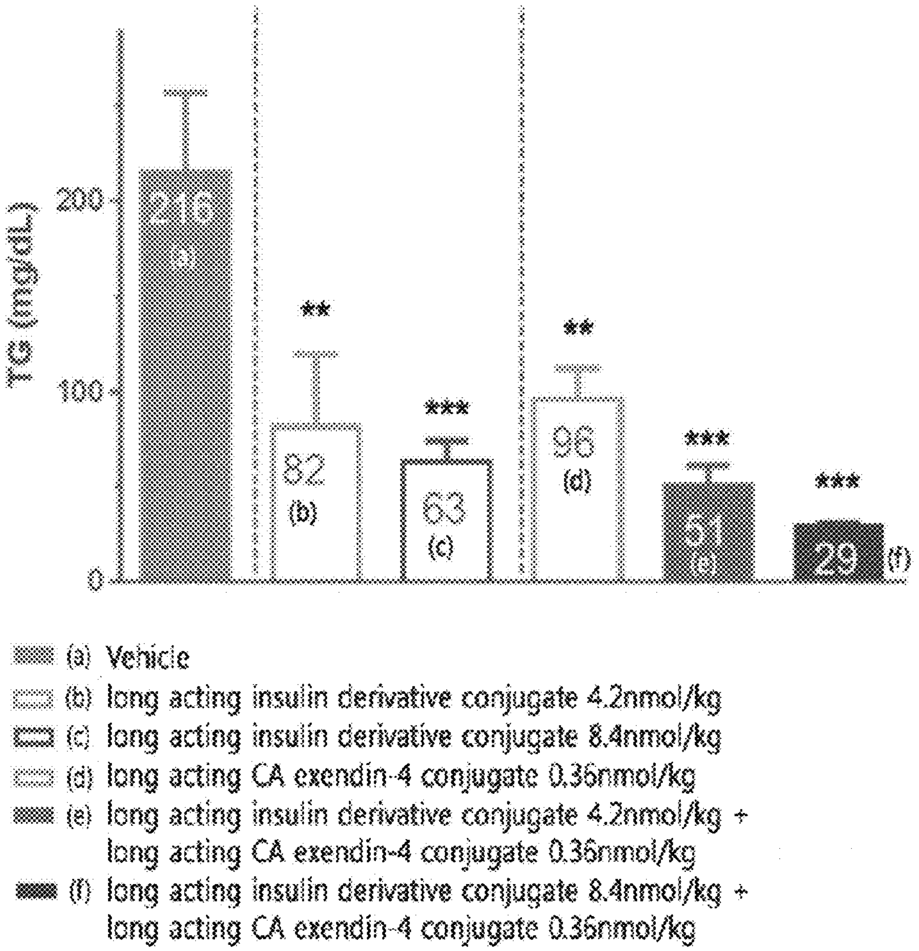
FIG. 4 is a graph showing the value of triglyceride in serum by 12-week combination administration of a long-acting insulin analogue conjugate and a long-acting exendin-4 conjugate to db/db (*P<0.05, P<0.01, *P<0.001 by ANOVA's test, vs. vehicle).

The concentration of triglyceride in serum was measured, and the results showed that, in a combination administration group of a long-acting insulin analogue conjugate and a long-acting exendin-4 conjugate, the concentration of triglyceride reduced in a dose-dependent manner (FIG. 4).

Figure 3:
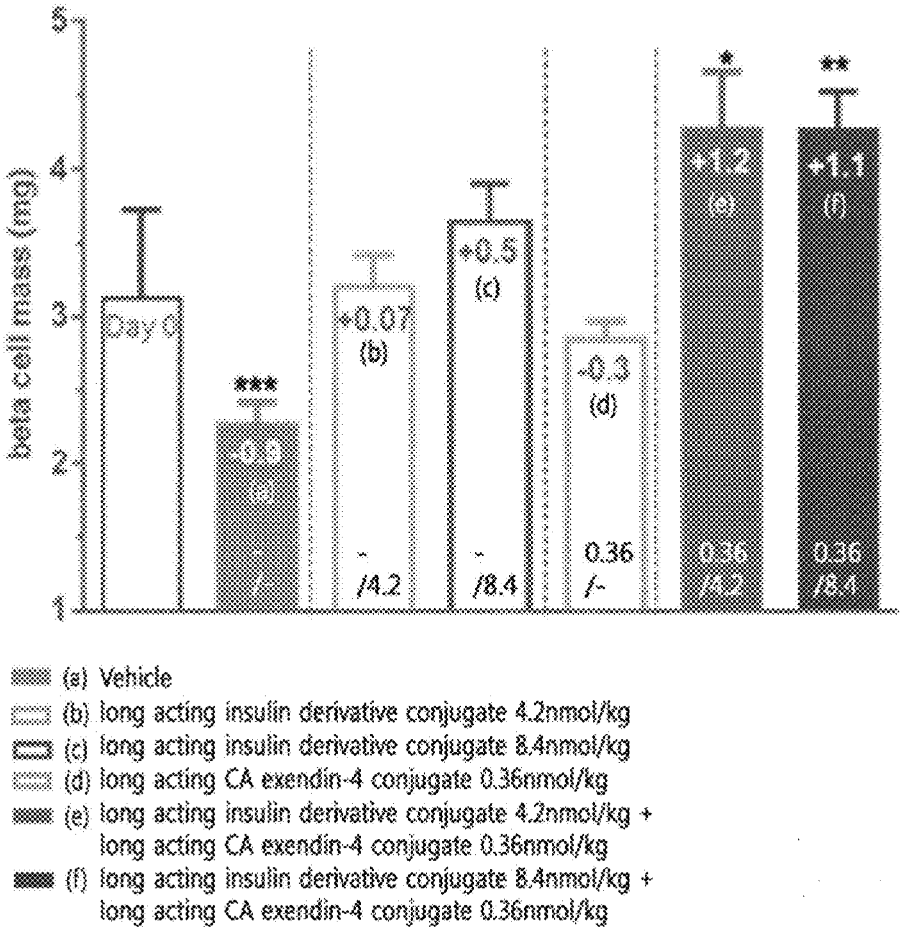
FIG. 3 is a graph numerically showing the effect of an increase in the beta cell mass by combination administration of a long-acting insulin analogue conjugate (a long-acting insulin derivative conjugate) and a long-acting exendin-4 conjugate to db/db (*P<0.05, P<0.01, *P<0.001 by ANOVA test, vs. vehicle).

The result of a comparison of the beta cell mass of each drug-treated group confirmed that a single-treated group of a long-acting insulin analogue conjugate, a single-treated group of a long-acting exendin-4 conjugate, and a combination administration group of the two conjugates exhibited increased beta cell mass as compared to the control group (FIG. 3). Further, as compared with a single-treated group of an a long-acting insulin analogue conjugate or a long-acting exendin-4 conjugate, the combination administration group of the two drugs showed synergistic effects. Based on these results, the lipotoxicity and the glucotoxicity were reduced by the combination administration of a long-acting insulin analogue conjugate and a long-acting exendin-4 conjugate.

These results show that combination administration of the long-acting insulin analogue conjugate and the long-acting exendin-4 conjugate of the present invention exhibits excellent effect of controlling blood glucose level and improving lipid in blood, compared to single administration thereof. The results suggests that the combination administration of the long-acting insulin analogue conjugate and the exendin-4 conjugate, which is a long-acting insulinotropic peptide, can retain beta cell mass and inhibit the progression of diabetes based on the improvement of lipotoxicity and glucotoxicity. In addition, the results suggest that a composite composition of the long-acting insulin analogue conjugate and the long-acting insulinotropic peptide conjugate according to the present invention, or combination administration of the two conjugates can significantly reduce the lipotoxicity associated with an increase in the lipid levels, and the glucotoxicity associated with an increase in blood glucose levels due to insufficient blood glucose control, which are side-effects that incur in some diabetic patients with a single administration of insulin or insulinotropic peptide, and further the progression of diabetes can be dramatically alleviated through the prevention of the abnormality in the function of pancreatic beta cells and/or the increase in the pancreatic beta cell mass, thus leading to improvement, treatment, prevention of diabetes and improvement of the prognosis of diabetes.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects and that all changes and modifications that are derived from the subject matter defined in the claims or equivalents thereof are intended to be embraced in the scope of the present invention.

The invention claimed is:

1. A method for treating diabetes mellitus comprising administering to a subject suffering from diabetes mellitus a composition comprising:

a long-acting insulin analogue conjugate in which an insulin analogue is linked to a biocompatible material capable of prolonging duration of activity of the insulin analogue via a linker or a covalent bond; and a long-acting insulinotropic peptide conjugate in which an insulinotropic peptide is linked to a biocompatible material capable of prolonging duration of activity of the insulinotropic peptide via a linker or a covalent bond, wherein the insulin analogue is characterized in having a variant selected from the group consisting of substitution, addition, deletion, modification and a combination thereof in one amino acid of a native insulin at a position selected from the group consisting of amino acids at positions 8, 12, 16, 24 and 25 of B chain and at positions 1, 2 and 16 of A chain.

2. The method according to claim 1, wherein the insulinotropic peptide is selected from the group consisting of GLP-1, exendin-3, exendin-4, agonists thereof, derivatives thereof, fragments thereof, variants thereof, and combinations thereof.

3. The method according to claim 2, wherein the insulinotropic peptide is an insulinotropic peptide derivative in which the N-terminal histidine residue of the insulinotropic peptide is substituted with a substance selected from the group consisting of des-amino-histidyl, dimethyl-histidyl, beta-hydroxy imidazopropionyl, 4-imidazoacetyl, and beta-carboxy imidazopropionyl.

4. The method according to claim 3, wherein the insulinotropic peptide is selected from the group consisting of a native exendin-4, an exendin-4 derivative in which the N-terminal amine group of exendin-4 is deleted, an exendin-4 derivative in which the N-terminal amine group of exendin-4 is substituted with a hydroxyl group, an exendin-4 derivative in which the N-terminal amine group of exendin-4 is modified with a dimethyl group, an exendin-4 derivative in which α-carbon of the first amino acid (histidine) of exendin-4 is deleted, an exendin-4 variant in which the $12^{th}$ amino acid (lysine) of exendin-4 is substituted with serine, and an exendin-4 variant in which the $12^{th}$ amino acid (lysine) of exendin-4 is substituted with arginine.

5. The method according to claim 1, wherein the biocompatible material is selected from the group consisting of polyethylene glycol, fatty acid, cholesterol, albumin and fragments thereof, albumin-binding materials, a polymer of repeating units of a particular amino acid sequence, antibodies, antibody fragments, FcRn binding material, in vivo connective tissues and derivatives thereof, nucleotides, fibronectin, transferrin, saccharides, and polymers.

6. The method according to claim 5, wherein the insulin analogue or the insulinotropic peptide is linked to the biocompatible material via a linker selected from the group consisting of polyethylene glycol, fatty acids, saccharides, polymers, low-molecular weight compounds, nucleotides, and combinations thereof.

7. The method according to claim 1, wherein the insulin analogue or the insulinotropic peptide is linked to the biocompatible material via a linker, and the biocompatible material is an FcRn binding material, wherein the linker is a peptide linker or a non-peptidyl linker selected from the group consisting of polyethylene glycol, polypropylene glycol, ethylene glycol-propylene glycol copolymer, polyoxyethylated polyol, polyvinyl alcohol, polysaccharide, dextran, polyvinyl ethyl ether, a biodegradable polymer, a lipid polymer, chitin, hyaluronic acid, and combinations thereof.

8. The method according to claim 7, wherein the FcRn binding material includes an immunoglobulin Fc region.

9. The method according to claim 8, wherein the immunoglobulin Fc region: is aglycosylated; is composed of one to four domains selected from the group consisting of CH1, CH2, CH3, and CH4 domains; includes a hinge region; is an Fc region derived from IgG, IgA, IgD, IgE, or IgM; is a hybrid of domains of different origins selected from the group consisting of IgG, IgA, IgD, IgE, and IgM; or is a dimer or a multimer composed of single-chain immunoglobulins consisting of domains of the same origin.

10. The method according to claim 7, wherein each end of the non-peptidyl linker respectively binds to the biocompatible material and an amine or thiol group of the insulin analogue or the insulinotropic peptide.

11. The method according to claim 1, wherein the composition further comprises a pharmaceutically acceptable carrier.

12. The method according to claim 1, wherein the long-acting insulin analogue conjugate and the long-acting insulinotropic peptide conjugate are administered simultaneously, sequentially, or reversely.

13. A method for reducing one or more pancreatic beta cell side-effects selected from the group consisting of lipotoxicity, glucotoxicity, abnormality in the function of pancreatic beta cells and reduction in the pancreatic beta cell mass in diabetic patients, comprising administering to a subject suffering from diabetes mellitus a composition comprising:

a long-acting insulin analogue conjugate in which an insulin analogue is linked to a biocompatible material capable of prolonging duration of activity of the insulin analogue via a linker or a covalent bond; and a long-acting insulinotropic peptide conjugate in which an insulinotropic peptide is linked to a biocompatible material capable of prolonging duration of activity of the insulinotropic peptide via a linker or a covalent bond, wherein the insulin analogue is characterized in having a variant selected from the group consisting of substitution, addition, deletion, modification and a combination thereof in one amino acid of a native insulin at a position selected from the group consisting of amino acids at positions 8, 12, 16, 24 and 25 of B chain and at positions 1, 2 and 16 of A chain.

14. The method according to claim 13, wherein the composition inhibits the progression of diabetes.

15. The method according to claim 13, wherein the composition improves diabetic prognosis of the subject suffering from diabetes mellitus.

16. A method for treating diabetes mellitus comprising administering to a subject suffering from diabetes mellitus a composition comprising:

a long-acting insulin analogue conjugate in which an insulin analogue is linked to a biocompatible material capable of prolonging duration of activity of the insulin analogue via a linker or a covalent bond; and a long-acting insulinotropic peptide conjugate in which an insulinotropic peptide is linked to a biocompatible material capable of prolonging duration of activity of the insulinotropic peptide via a linker or a covalent bond, wherein the insulin analogue is characterized in having a substitution in one amino acid of a native insulin at the position selected from the group consisting of positions 8 and 23 to 25 of the B chain of native insulin, and 1, 2, 14 and 19 of the A chain of native insulin is substituted with other amino acid, wherein the amino acid at position of 8 of the B chain is substituted with alanine; the amino acid at position of 23 of the B chain is substituted with alanine; the amino acid at position of 24 of the B chain is substituted with alanine; the amino acid at position of 25 of the B chain is substituted with alanine; the amino acid at position of 1 of the A chain is substituted with alanine; the amino acid at position of 2 of the A chain is substituted with alanine; the amino acid at position of 14 of the A chain is substituted with glutamic acid or asparagine; or the amino acid at position of 19 of the A chain is substituted with alanine.

17. The method according to claim 16, wherein the insulin analogue comprises the amino acid sequence selected from the group consisting of SEQ ID Nos. 20, 22, 24, 26, 28, 30, 32, 34 and 36.

18. The method according to claim 16, wherein the long-acting insulin analogue conjugate is characterized that an insulin analogue in which an amino acid at position 14 of A chain of insulin is substituted with glutamic acid, is linked to an immunoglobulin Fc region via a non-peptidyl polymer as a linker, and the long-acting insulinotropic peptide conjugate is characterized that an imidazo-acetyl exendin-4 as insulinotropic peptide is linked to an immunoglobulin Fc region via a non-peptidyl polymer as a linker.

19. A method for preparing a drug for treating diabetes mellitus, comprising:

a long-acting insulin analogue conjugate in which an insulin analogue is linked to a biocompatible material capable of prolonging duration of activity of insulin analogue via a linker or a covalent bond; and a long-acting insulinotropic peptide conjugate in which an insulinotropic peptide is linked to a biocompatible material capable of prolonging duration of activity of insulinotropic peptide via a linker or a covalent bond, wherein the insulin analogue is characterized in having a variant selected from the group consisting of substitution, addition, deletion, modification and combinations thereof in one amino acid of a native insulin at a position selected from the group consisting of amino acids at positions 8, 12, 16, 24 and 25 of B chain and at positions 1, 2 and 16 of A chain.

20. A method for reducing one or more pancreatic beta cell side-effects selected from the group consisting of lipotoxicity, glucotoxicity, abnormality in the function of pancreatic beta cells and reduction in the pancreatic beta cell mass in diabetic patients, comprising administering to a subject suffering from diabetes mellitus a composition comprising:

a long-acting insulin analogue conjugate in which an insulin analogue is linked to a biocompatible material capable of prolonging duration of activity of the insulin analogue via a linker or a covalent bond; and a long-acting insulinotropic peptide conjugate in which an insulinotropic peptide is linked to a biocompatible material capable of prolonging duration of activity of the insulinotropic peptide via a linker or a covalent bond, wherein the insulin analogue is characterized in having a substitution in one amino acid of a native insulin at the position selected from the group consisting of positions 8 and 23 to 25 of the B chain of native insulin, and 1, 2, 14 and 19 of the A chain of native insulin is substituted with other amino acid, wherein the amino acid at position of 8 of the B chain is substituted with alanine; the amino acid at position of 23 of the B chain is substituted with alanine; the amino acid at position of 24 of the B chain is substituted with alanine; the amino acid at position of 25 of the B chain is substituted with alanine; the amino acid at position of 1 of the A chain is substituted with alanine; the amino acid at position of 2 of the A chain is substituted with alanine; the amino acid at position of 14 of the A chain is substituted with glutamic acid or asparagine; or the amino acid at position of 19 of the A chain is substituted with alanine.

21. A method for preparing a drug for treating diabetes mellitus, comprising a long-acting insulin analogue conjugate in which an insulin analogue is linked to a biocompatible material capable of prolonging duration of activity of insulin analogue via a linker or a covalent bond; and a long-acting insulinotropic peptide conjugate in which an insulinotropic peptide is linked to a biocompatible material capable of prolonging duration of activity of insulinotropic peptide via a linker or a covalent bond, wherein the insulin analogue is characterized in having a substitution in one amino acid of a native insulin at the position selected from the group consisting of positions 8 and 23 to 25 of the B chain of native insulin, and 1, 2, 14 and 19 of the A chain of native insulin is substituted with other amino acid, wherein the amino acid at position of 8 of the B chain is substituted with alanine; the amino acid at position of 23 of the B chain is substituted with alanine; the amino acid at position of 24 of the B chain is substituted with alanine; the amino acid at position of 25 of the B chain is substituted with alanine; the amino acid at position of 1 of the A chain is substituted with alanine; the amino acid at position of 2 of the A chain is substituted with alanine; the amino acid at position of 14 of the A chain is substituted with glutamic acid or asparagine; or the amino acid at position of 19 of the A chain is substituted with alanine.

* * * * *